US010752876B2

(12) United States Patent
Thompson et al.

(10) Patent No.: US 10,752,876 B2
(45) Date of Patent: Aug. 25, 2020

(54) ENHANCED THERMAL STABILITY FOR ADENOVIRAL VECTORS THROUGH SPRAY DRYING

(71) Applicant: MCMASTER UNIVERSITY, Hamilton (CA)

(72) Inventors: Michael Thompson, Hamilton (CA); Zhou Xing, Ancaster (CA); Daniel Adam LeClair, Innisfil (CA); Emily Cranston, Dundas (CA)

(73) Assignee: McMaster University, Hamilton (CA)

( * ) Notice: Subject to any disclaimer, the term of this patent is extended or adjusted under 35 U.S.C. 154(b) by 140 days.

(21) Appl. No.: 15/757,033

(22) PCT Filed: Sep. 2, 2016

(86) PCT No.: PCT/CA2016/051046
§ 371 (c)(1),
(2) Date: Mar. 2, 2018

(87) PCT Pub. No.: WO2017/035664
PCT Pub. Date: Mar. 9, 2017

(65) Prior Publication Data
US 2019/0062692 A1  Feb. 28, 2019

Related U.S. Application Data

(60) Provisional application No. 62/213,148, filed on Sep. 2, 2015.

(51) Int. Cl.
C07K 16/24 (2006.01)
A61K 39/00 (2006.01)
A61K 39/395 (2006.01)
C07K 16/00 (2006.01)
A61K 38/17 (2006.01)
C12N 1/04 (2006.01)
C12N 15/86 (2006.01)
C12N 7/00 (2006.01)
A61K 9/00 (2006.01)
A61K 9/16 (2006.01)
A61K 39/235 (2006.01)
A61K 48/00 (2006.01)

(52) U.S. Cl.
CPC .............. C12N 1/04 (2013.01); A61K 9/0019 (2013.01); A61K 9/1623 (2013.01); A61K 9/1652 (2013.01); A61K 9/1682 (2013.01); A61K 39/235 (2013.01); C12N 7/00 (2013.01); C12N 15/86 (2013.01); A61K 48/00 (2013.01); A61K 2039/5256 (2013.01); A61K 2039/5258 (2013.01); C12N 2710/10334 (2013.01); C12N 2710/10343 (2013.01); C12N 2710/10351 (2013.01)

(58) Field of Classification Search
CPC .............. C07K 16/241; C07K 2317/14; C07K 2317/21; A61K 39/39591; A61K 47/183
See application file for complete search history.

(56) References Cited

U.S. PATENT DOCUMENTS

| | | | |
|---|---|---|---|
| 6,689,600 B1 | 2/2004 | Wu et al. | |
| 7,888,096 B2 | 2/2011 | Wu et al. | |
| 7,888,097 B2 | 2/2011 | Wu et al. | |
| 2012/0058162 A1* | 3/2012 | Jin | A61K 39/12 424/400 |

FOREIGN PATENT DOCUMENTS

WO    2008114021 A1    9/2008

OTHER PUBLICATIONS

Jin TH et al., "Stabilizing Formulations for Inhalable Powders of an Adenovirus 35-Vectored Tuberculosis (TB) Vaccine (AERAS-402)", Vaccine, 28; Jun. 17, 2010, ISSN: 0264-410X.

Maa YF et al., "Influenza Vaccine Powder Formulation Development: Spray-Freeze-Drying and Stability Evaluation," Journal of Pharmaceutical Sciences, 93(7), pp. 1912-1923; Jul. 1, 2004, ISSN: 0022-3549.

Wold, WSM et al., "Adenovirus Vectors for Gene Therapy, Vaccination and Cancer Gene Therapy", Current Gene Therapy, 13(6), pp. 421-443; Dec. 2013, ISSN: 1566-5232.

LeClair DA et al., "Evaluation of Excipients for Enhanced Thermal Stabilization of a Human Type 5 Adenoviral Vector Through spray Drying", International Journal of Pharmaceutics, 506(1), pp. 289-301; Jun. 15, 2016, epub Apr. 26, 2016, ISSN:0378-5173.

LeClair DA et al., "Optimization of Spray Drying Conditions for Yield, Particle Size and Biological Activity of Thermally Stable Viral Vectors", Pharmaceutical Research, 33(11); epub Jul. 22, 2016, ISSN: 1573-904X.

Kanojia G. et al., "A Design of Experiment Approach to Predict Product and Process Parameters for a Spray Dried Influenza Vaccine", International Journal of Pharmaceutics, 511(2), pp. 1098-1111; epub Aug. 16, 2016, ISSN: 1873-3476.

(Continued)

Primary Examiner — Barry A Chestnut
(74) Attorney, Agent, or Firm — Bereskin & Parr LLP/S.E.N.C.R.L., S.R.L.

(57) ABSTRACT

The present application includes stabilized adenovirus compositions comprising an adenovirus and an excipient, wherein the excipient comprises a mixture of dextran and mannitol in amounts effective to maintain at least 40% of the adenovirus activity after spray drying.

19 Claims, 15 Drawing Sheets

(56) References Cited

OTHER PUBLICATIONS

Saboo S. et al., "Optimized Formulation of a Thermostable Spray-Dried Virus-Like Particle Vaccine Against Human Papillomavirus", Molecular Pharmaceutics, 13(5), pp. 1646-1655; Apr. 11, 2016, ISSN: 1543-8392.
ISR and Written Opinion of corresponding PCT Application No. PCT/CA2016/051046.
International Preliminary Report on Patentability of corresponding PCT Application No. PCT/CA2016/051046.

* cited by examiner a.

b.

c.

ENHANCED THERMAL STABILITY FOR ADENOVIRAL VECTORS THROUGH SPRAY DRYING

CROSS REFERENCE TO RELATED APPLICATIONS

This application is a National Stage of International Application No. PCT/CA2016/051046 filed on Sep. 2, 2016 which claims the benefit of priority from U.S. provisional patent application No. 62/213,148 filed on Sep. 2, 2015, the contents of both of which are incorporated herein by reference in their entirety.

FIELD

The present application relates to stabilized adenoviral compositions and methods of preparation and use thereof.

BACKGROUND

Adenovirus-based gene transfer vectors have been increasingly developed as vaccine platforms against both old and newly emerging infections.[1-3] However, the real world application of adenoviral vectors, in particular in the developing countries, is limited by their instability when stored or transported at even mild temperatures. Alteration of genetic data within viral genomes for vaccine vector applications results in an increased instability in maintaining infectious function.[4,5] Storage of these vectors within synthetic vials furthermore accelerates denaturing of proteins and loss of viral infectivity through aggregation. Thus, to maintain function, adenoviral vectors suspended in an aqueous medium require storage at temperatures close to −80° C. to maintain 'cold chain' protocols.[6] This condition inhibits molecular movements of the stored adenoviruses, hindering their aggregation.[7-9] Immobilization of viral vectors within cold storage conditions is uneconomical, and potentially infeasible in areas around the globe requiring vaccination the most.

A major goal for both the World Health Organization and Bill & Melinda Gates Foundation is to alleviate cold chain requirements for vaccine storage and distribution.[10] Hence, thermal stability, as used in reference to new classes of vaccines, refers to the ability of a viral vector to be stored at elevated temperatures (above −80° C.) for prolonged duration without significant loss of activity. A promising approach capable of increasing thermal stability of labile vectors is through their dispersion within the amorphous phase of a solid matrix, termed as vitrification.[8,11] Vitrification of viral vectors within sugars, polymers, amino acids, surfactants, and other materials has maintained viral activity at storage temperatures above typical cold chain temperatures.[12-14]

Previous studies have shown the relationship between matrix physical and chemical properties on thermal stability of entrapped species.[15] The production of a solid matrix is known to greatly hinder the molecular movements of an entrapped adenoviral vector, thus preventing unfolding and aggregation[16]. Selection of a purely amorphous matrix may result in a solid with high moisture sensitivity[17] which will reduce stabilization of any dispersed labile biological materials.[18] Conversely, crystalline structures are moisture-resistant but not optimal for stabilizing dispersed biological materials due to poor incorporation within the matrix. Binary excipient mixtures are a novel consideration for stabilizing viral vectors since they can be used to balance the amorphous and crystalline phases of a formulation,[19,20] though no current examples are systematically evaluated within the literature. Semicrystalline materials may offer increased thermal stability and moisture resistivity over their amorphous counterparts. Previous publications have demonstrated that crystalline regions can act as physical barriers for molecular movements and water sorption.[21-23]

Several drying processes such as spray drying, freeze drying and foam drying have been employed in recent years for producing dry powder forms of solid viral vector dispersions.[24-26] Spray drying is increasingly preferred since its simple requirements facilitate product scalability[27] and favorable economics. During spray drying, a pressurized gas is used to disperse a liquid feed into small droplets within a drying chamber. Evaporation of heated aqueous droplets results in precipitation of the dissolved solutes and suspended materials. Current research aimed at improving thermal stability for labile biological materials has shown great success with spray drying vaccines ranging from attenuated pathogens to antigen-based formulations.[24-26,28,29] The degree of thermal stabilization varies significantly depending on the dispersed biological material. For example, a spray dried bacillus Calmette-Guérin vaccine formulation with L-leucine demonstrated a minimal activity loss of approximately 2.0 log after 120 days at 25° C. under high moisture protection.[24] Alternatively, an antigen-based influenza subunit vaccine stabilized in inulin retained considerable immunogenicity for up to three years of storage at 20° C.[29] The variance in stability among spray dried biological materials emphasizes the need for specific evaluation of each vaccine backbone and excipient combination.

Human adenovirus type 5 (AdHu5) has been shown to be an effective vaccine vector for prevention of infectious diseases and has been developed in both liquid buffer and lyophilized forms.[30,31] Current limitations to AdHu5 use stem from pre-existing AdHu5 immunity and the lack of a thermally stabilized form. It is estimated that 30-100% of the population, depending on geographical location, have been exposed to AdHu5 and therefore elicit an AdHu5-specific response upon infection.[32] The anti-AdHu5 immunity pre-existing in most of the human population poses a potential limitation to the application of AdHu5-vectored vaccines. However, the results from a recent clinical vaccine trial suggest that the potency of AdHu5 vector system is able to diminish the negative effect of a pre-existing immunity.[30] Furthermore, AdHu5 vector is particularly amenable to vaccination via the respiratory mucosal route against lung infectious diseases and the human respiratory tract has been found to have minimal pre-existing anti-AdHu5 immunity.[33] Thus, an AdHu5-based vaccine is expected to be even more effective when given via the respiratory mucosal route versus a parenteral route. In terms of thermal stability, AdHu5 has yet to be developed into a well-stabilized spray dried form.

SUMMARY

The present application discloses the production of thermally stable adenoviral formulations through spray drying with non-cytotoxic excipients. More specifically, the present application reports a study of binary sugar and amino acid excipient matrices to observe the effects on adenovirus stability. The effects of storage time, temperature and humidity were systematically examined on spray dried vector infectivity. Through this work, a thermally stable spray dried adenovirus formulation has been developed.

Accordingly, the present application includes an adenovirus composition comprising adenovirus particles and an excipient, wherein the excipient comprises a mixture of dextran and mannitol in amounts effective to maintain at least 40% of the adenovirus activity after spray drying.

In some embodiments, the spray dried adenovirus compositions of the application are combined with a pharmaceutically acceptable carrier for administration to a cell in vitro or to a subject in vivo. Accordingly the present application includes a pharmaceutical composition comprising an adenovirus composition of the application and one or more pharmaceutically acceptable carriers. In some embodiments, the pharmaceutical composition is a vaccine composition.

The present application also includes a method for preparing a stabilized adenovirus composition comprising:

a) combining the adenovirus with an aqueous solution comprising an excipient, wherein the excipient comprises a mixture of dextran and mannitol in amounts effective to maintain at least 40% of the adenovirus activity after spray drying to provide a mixture; and b) spray drying the mixture to provide the stabilized adenovirus composition.

The above method provides spray dried compositions of the application. The present application further includes a method for delivering or transferring one or more nucleic acid sequences to target cells comprising administering an effective amount of a spray dried composition of the application to the cells. In some embodiments the nucleic acid sequence comprises one or more genes to be expressed in the cell or subject. Therefore present application also includes a method for gene therapy comprising administering an effective amount of a spray dried composition of the application to a subject in need thereof.

In some embodiments, the application includes a use of a spray dried composition of the application for delivering or transferring one or more nucleic acid sequences to target cells. In further embodiments the application includes the use of a spray dried composition of the application for gene therapy.

The present application also include a method of preparing a vaccine composition comprising:

a) combining the adenovirus with an aqueous solution comprising an excipient, wherein the excipient comprises a mixture of dextran and mannitol in amounts effective to maintain at least 40% of the adenovirus activity after spray drying to provide a mixture;

b) optionally adding one or more of an adjuvant, buffer, antibiotic and/or additive to the mixture; and c) spray drying the mixture.

In some embodiments, the method of preparing a vaccine composition further comprises reconstituting the spray dried mixture in a liquid suitable for vaccine formulations.

In some embodiment, the application also includes a method of stabilizing adenoviral vectors comprising dispersing the adenoviral vector in a binary sugar mixture, then spray drying the resulting formulation. In some embodiments, the binary sugar mixture is mannitol and dextran. In some embodiments the ratio of mannitol to dextran is 2:1 by weight. In some embodiments, the adenoviral vectors are of human, chimpanzee or other animal origin. In some embodiments, the present application also includes a formulation produced by the methods disclosed herein, wherein the resulting powder is delivered as a vaccine inhalation.

This work in the present application extends the possible applications of AdHu5 as a vaccine by producing a more thermally stable vector through spray drying with non-cytotoxic excipients. A thermally stable spray dried AdHu5 vector in a mannitol dextran matrix has been prepared and the physical properties desirable for the best stabilization have been found, which can be used to further the field of dry powder vector development. The method can be applied to other adenoviral vectors, including those from non-human sources, and can also be used to produce a dry powder inhalable vaccine.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

The embodiments of the application will now be described in greater detail with reference to the attached drawings in which.

DETAILED DESCRIPTION

I. Definitions

Figure 1:
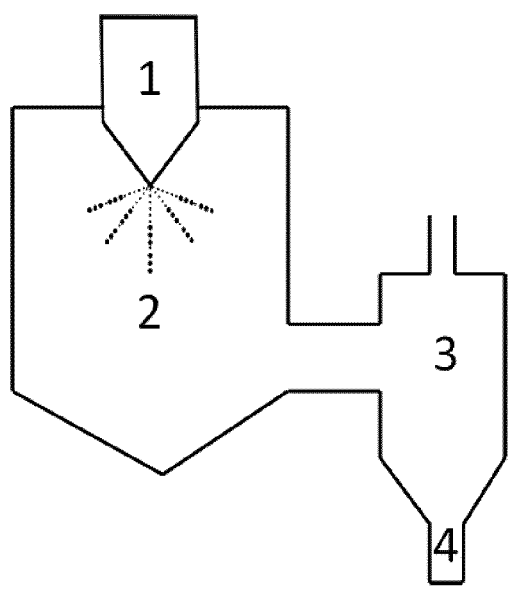
FIG. 1 shows a schematic diagram of the general spray drying process. Labeled components are the spray dryer nozzle (1), the spray drying chamber (2), the separating cyclone (3) and the collection chamber (4).

Unless otherwise indicated, the definitions and embodiments described in this and other sections are intended to be applicable to all embodiments and aspects of the present application herein described for which they are suitable as would be understood by a person skilled in the art.

As used herein in this specification and the appended claims, the singular forms "a", "an" and "the" include plural references unless the content clearly dictates otherwise. Thus for example, a composition containing "an excipient" includes one such excipient or a mixture of two or more excipients.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this application and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "and/or" as used herein means that the listed items are present, or used, individually or in combination. In effect, this term means that "at least one of" or "one or more" of the listed items is used or present.

The term "suitable" as used herein means that the selection of the particular compound or conditions would depend on the specific requirements to be satisfied, but the selection would be well within the skill of a person trained in the art.

The term "excipient" as used herein refers to any ingredient in a composition, in particular a pharmaceutical or vaccine composition, other than the active ingredient.

The term "spray dry" or "spray dried" or "spray drying" refers to a method of producing a dry powder from a liquid or slurry by rapidly drying with a hot gas. The liquid or slurry is sprayed through a nozzle into a chamber that simultaneously has hot air being blow in. As droplets of the solution are released through the nozzle and come in contact with the hot air, the moisture content of each droplet is removed, producing a powder.

The term "stabilized adenovirus" or "stabilized adenovirus composition" as used herein refers to an adenovirus that maintains infectivity over a longer period of time than one that is not stabilized. For example, incubation of an adenovirus without an excipient results in a loss in infectivity over time. However, a stabilized adenovirus will retain more of its infectivity in the presence of a stabilizing agent. A loss of viral infectivity can also occur by exposing the adenovirus to particular chemicals or by processing, such as by concentrating or storing the adenovirus. A stabilized adenovirus as disclosed herein can resist loss of viral infectivity to at least one type of treatment.

The term "composition of the application" or "adenovirus composition of the application" as used herein refers to a composition comprising at least an adenovirus and an excipient, wherein the excipient comprises a mixture of dextran and mannitol in amounts effective to maintain at least 40% of the adenovirus activity after spray drying.

The term "adenovirus" refers to the virus itself or derivatives thereof. The term covers all serotypes and subtypes and both naturally occurring and recombinant forms, except where indicated otherwise. Any subtype, mixture of subtypes, or chimeric adenovirus can be used as the source of the viral genome for the adenoviral vector.

An "adenovirus vector" or "adenoviral vector" (used interchangeably) is a term well understood in the art and generally comprises all or a portions of an adenovirus genome. It generally refers to an infectious unit comprising information necessary for viral replication in a susceptible host cell or can be a replication incompetent adenovirus that lacks critical genetic information needed for replication. A recombinant adenovirus that contains one or more foreign nucleic acid molecules or genes modified by recombinant DNA techniques is also included within the meaning of an adenovirus.

By "replication-deficient" is meant that the recombinant adenoviral vector comprises an adenoviral genome that lacks at least one replication-essential gene function (i.e., such that the recombinant adenoviral vector does not replicate in typical host cells, especially those in the human patient that could be infected by the recombinant adenoviral vector in the course of treatment in accordance with the invention).

The term "treating" or "treatment" as used herein and as is well understood in the art, means an approach for obtaining beneficial or desired results, including clinical results. Beneficial or desired clinical results can include, but are not limited to alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. "Treating" and "treatment" as used herein also include prophylactic treatment. For example, a subject with a disease or condition that can be treated to prevent progression with a composition described herein to prevent recurrence. Treatment methods comprise administering to a subject a therapeutically effective amount of a composition of the application and optionally consist of a single administration, or alternatively comprise a series of administrations. For example, the compositions of the application may be administered at least once a week. However, in another embodiment, the compositions may be administered to the subject from about one time per three weeks, or about one time per week to about once daily for a given treatment. In another embodiment, the compounds are administered 2, 3, 4, 5 or 6 times daily. The length of the treatment period depends on a variety of factors, such as the severity of the disease, disorder or condition, the age of the subject, the concentration and/or the activity of the compositions of the application, and/or a combination thereof. Changes in dosage may result and become apparent by standard diagnostic assays known in the art. In some instances, chronic administration may be required. For example, the compounds are administered to the subject in an amount and for duration sufficient to treat the patient.

As used herein, the term "therapeutically effective amount" means an amount effective, at dosages and for periods of time necessary to achieve the desired result. Therapeutically effective amounts may vary according to factors such as the disease state, age, sex and/or weight of the subject. The amount of a given composition that will correspond to such an amount will vary depending upon various factors, such as the given active agent, the pharmaceutical formulation, the route of administration, the type of condition, disease or disorder, the identity of the subject being treated, and the like, but can nevertheless be routinely determined by one skilled in the art.

The term "administered" as used herein means administration of a therapeutically effective amount of a composition of the application to a cell either in cell culture or in a subject.

The term "pharmaceutically acceptable" means compatible with the treatment of subjects, for example humans.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to a subject.

The term "mammal" or "mammalian" is intended to synonymous with animal and includes, but not to be limited to bovine, porcine, feline, simian, canine, equine, murine, rat or human.

II. Compositions of the Application

The present application reports the production of adenovirus compositions having improved thermal stability through spray drying using non-cytotoxic excipients.

In another aspect, the present application provides formulations which enhance the physical stability of adenovirus vectors even under harsh storage conditions.

The present Applicants have discovered a specific combination of non-toxic sugars, namely mannitol and dextran, that provides enhanced stability for adenoviruses that have been spray dried, said stability lasting through storage at ambient temperatures. This combination of sugars provided unique and surprising storage-enhancing properties that were not found with other combinations of sugars or with an amino acid known to be used as an excipient in spray dry compositions.

Accordingly, in one of its aspects, the present application includes an adenovirus composition comprising adenovirus particles and an excipient, wherein the excipient comprises a mixture of dextran and mannitol in amounts effective to maintain at least 40% of the adenovirus activity after spray drying.

The compositions described herein are useful for a variety of adenoviruses, which may be readily selected by one of skill in the art. In some embodiments, the adenovirus is a recombinant adenovirus. In some embodiments, the recombinant adenovirus is a DNA adenovirus. In some embodiments, the adenovirus is of mammalian origin. In some embodiments, the mammal is human or a simian. In some embodiments, the adenovirus is replication-deficient. In some embodiments, the adenovirus is a human adenovirus A, B, C, D, E or F, including for example, Ad5, Ad2, Ad6 and Ad24 serotypes. In some embodiments the adenovirus is human Ad5. In some embodiments the adenovirus is simian Ad5. In some embodiments, the adenovirus is from a chimpanzee, such as chimpanzee Ad5. The use of simian-derived adenoviral vaccine vectors advantageously avoids the issue of anti-AdHu5 immunity that may be present in some humans (see M. Jeyanathan, N. Thanthrige-Don, S. Afkhami, R. Lai, D. Damjanovic, A. Zganiacz, X. Feng, X-D. Yao, K. L. Rosenthal, M. Fe Medina, J. Gauldie, H. C. Ertl, and Z. Xing. Novel chimpanzee adenovirus-vectored respiratory mucosal tuberculosis vaccine: Overcoming local anti-human adenovirus immunity for potent TB protection. *Mucosal Immunol* 8:1373-1387, 2015).

In some embodiments, the adenovirus is comprised in a vector. In some embodiments the vector comprises nucleic acids, including complete genes, to be transferred to host cells, using in vitro or in vivo delivery methods.

In some embodiments, the excipient comprises a mixture of dextran and mannitol in amounts effective to maintain at least 40%, 50% or 60% of the adenovirus activity after spray drying.

In some embodiments, the excipient comprises a mixture of dextran and mannitol in amounts effective to maintain at least 10%, 20% or 30% of the adenovirus activity after spray drying and storage at 20° C., less than 10% relative humidity (RH) and for at least 90 days.

In some embodiments, the excipient comprises about 60 wt % to about 75 wt % of the mannitol. In some embodiments, the excipient comprises about 25 wt % to about 40 wt % dextran. In some embodiments, the excipient comprises about 66 wt % mannitol and about 33 wt % dextran.

In some embodiments, the adenovirus composition is a pharmaceutical composition. In some embodiments the adenovirus composition is a vaccine composition. In some embodiments, the adenovirus composition has been spray dried.

In some embodiments, the adenovirus composition has a moisture uptake of <10% when stored at 20° C., <10% RH and for 20 days.

In some embodiments, the change in adenovirus infectivity following spray drying of the adenovirus compositions of the application and storage at 20° C., <10% RH and for 90 days is less than 1.0 log unit.

In some embodiments, the spray dried adenovirus compositions of the application are combined with a pharmaceutically acceptable carrier for administration to a cell in vitro or to a subject in vivo. Accordingly the present application includes a pharmaceutical composition comprising an adenovirus composition the application and one or more pharmaceutically acceptable carriers.

In some embodiments, the spray dried adenovirus compositions of the application are combined with a pharmaceutically acceptable vaccine carrier for administration to a cell in vitro or to a subject in vivo. Accordingly the present application includes a vaccine composition comprising an adenovirus composition the application and one or more pharmaceutically acceptable vaccine carriers.

In some embodiments, the spray dried adenovirus compositions are maintained at a temperature above 0° C., or at 4° C. or higher (e.g., 4-10° C.). In some embodiments, it is desirable to maintain the adenovirus compositions at a temperature of 10° C. or higher (e.g., 10-20° C.), 20° C. or higher (e.g., 20-25° C.), or even 30° C. or higher (e.g., 30-40° C.). In some embodiments, the adenovirus compositions are maintained at the aforementioned temperature(s) for at least 1 day (e.g., 7 days or more), though typically the time period will be longer, such as at least 3, 4, 5, or 6 weeks, or even longer, such as at least 10, 11, or 12 weeks or up to 4, 5 or 6 months, prior to use, for example, administration to a cell or a subject.

During that time period, the adenovirus optimally loses no, or substantially no, activity, although some loss of activity is acceptable, especially with relatively higher storage temperatures and/or relatively longer storage times. The activity of the adenoviral vector composition desirably decreases about 40% or less, about 50% or less or about 60% or less, after any of the aforementioned time periods.

In some embodiments, a pharmaceutical composition comprising an adenovirus composition of the application comprises additional therapeutic or biologically-active agents. For example, therapeutic factors useful in the treatment of a particular indication are present.

In some embodiments, the compositions of the application contain conventional pharmaceutical ingredients, such as, but not limited to preservatives, carbohydrates, stabilizers and/or surfactants.

III. Methods and Uses of the Application

The present application also includes a method for preparing a stabilized adenovirus composition comprising:

a) combining the adenovirus with an aqueous solution comprising an excipient, wherein the excipient comprises a mixture of dextran and mannitol in amounts effective to maintain at least 40% of the adenovirus activity after spray drying to provide a mixture; and b) spray drying the mixture to provide the stabilized adenovirus composition.

In some embodiments, the aqueous solution comprising the excipient is prepared by dissolving the dextran and mannitol in an aqueous solution, for example using water suitable for administration to subjects including humans and for example at a concentration in the range of about 0.1 mg excipient per mL of water to about 10 mg excipient per mL of water, about 0.5 mg excipient per mL of water to about 5 mg excipient per mL of water or about 1 mg excipient per mL of water. In some embodiments, the aqueous solution comprising the excipient has a pH of about 6 to about 7, or about 6.5.

In some embodiments the spray drying is performed using a spray gas flow rate of about 400 to about 500 L/h, an inlet temperature of about 110° C. to about 130° C., an outlet temperature of about 50° C. to about 80° C. and an feed flow rate of about 200 mL/h to about 250 mL/h. In some embodiments the spray drying is performed using a spray gas flow rate of about 430 to about 440 L/h, an inlet temperature of about 115° C. to about 125° C., an outlet temperature of about 60° C. to about 70° C. and an feed flow rate of about 210 mL/h to about 220 mL/h.

Optimization of spray drying conditions for yield, particle size and biological activity of the thermally stable adenoviral vectors can be done using methods known in the art, for example as described in Applicant's own publication: LeClair D A, Cranston E D, Xing Z, and Thompson M R' *Pharmaceutical Research*, e-published on Jul. 22, 2016.

In some embodiments, the excipient comprises a mixture of dextran and mannitol in amounts effective to maintain at least 40%, 50% or 60% of the adenovirus activity after spray drying.

In some embodiments, the excipient comprises a mixture of dextran and mannitol in amounts effective to maintain at least 10%, 20% or 30% of the adenovirus activity after spray drying and storage at 20° C., less than 10% relative humidity (RH) and for at least 90 days.

In some embodiments, the excipient comprises about 60 wt % to about 75 wt % of the mannitol. In some embodiments, the excipient comprises about 25 wt % to about 40 wt % dextran. In some embodiments, the excipient comprises about 66 wt % mannitol and about 33 wt % dextran.

In some embodiments, the method for preparing a stabilized adenovirus composition further comprises storing the stabilized adenovirus composition at temperature above cold-chain storage (−80° C.), for example at a temperature above 0° C., or at 4° C. or higher (e.g., 4-10° C.). In some embodiments, the stabilized adenovirus composition is stored at a temperature of 10° C. or higher (e.g., 10-20° C.), 20° C. or higher (e.g., 20-25° C.), or even 30° C. or higher (e.g., 30-40° C.). In some embodiments, the stabilized adenovirus composition is maintained at the aforementioned temperature(s) for at least 1 day (e.g., 7 days or more), though typically the time period will be longer, such as at least 3, 4, 5, or 6 weeks, or even longer, such as at least 10, 11, or 12 weeks or up to 4, 5 or 6 months, prior to use, for example, administration to a cell or a subject.

In some embodiments, the stabilized adenovirus composition has a moisture uptake of <10% when stored at 20° C., <10% RH and for 20 days.

In some embodiments, the change in adenovirus infectivity following spray drying and storage at 20° C., <10% RH and for 90 days is less than 1.0 log unit.

In some embodiments, the method for preparing a stabilized adenovirus composition further comprises the step of processing the stabilized adenovirus composition into a formulation suitable for administration as a liquid injection. In further embodiments, the method further comprises the step of processing the stabilized adenovirus composition into a formulation suitable for administration via ingestion or via pulmonary delivery. In further embodiments, the method further comprises the step of processing the stabilized adenovirus composition into a formulation suitable for administration via inhalation.

The present application also includes various therapeutic methods uses of the compositions of the application, for example for gene transfer or as vaccines.

Therefore, in some embodiments, the spray-dried adenovirus compositions of the application find use as a vaccine. Accordingly the present application also includes a use of the spray-dried adenovirus compositions of the application as a vaccine and a method for treating a subject with a vaccine comprising administering an effective amount of the spray-dried adenovirus compositions of the application to a subject in need thereof. In some embodiments, the adenovirus compositions further comprises one or more of an adjuvant, buffer, antibiotic and additive.

In some embodiments, spray-dried adenovirus particles such as whole killed adenovirus, live attenuated adenovirus, chemically inactivated adenovirus or live adenoviral vectors are suitable for use as a vaccine. In some embodiments, the spray-dried adenovirus particles are used as antigens or to encode antigens such as viral proteins for the treatment or prevention of a number of conditions including but not limited to viral infection, sequelae of viral infection including but not limited to viral-induced toxicity, cancer and allergies. Such antigens contain one or more epitopes that will stimulate a host's immune system to generate a humoral and/or cellular antigen-specific response. In some embodiments, the vaccine is a subunit, conjugate or multivalent vaccine.

In some embodiments, the vaccine compositions of the present application further comprise appropriate buffers and additives such as antibiotics, adjuvants or other molecules that enhance presentation of vaccine antigens to specific cells of the immune system. A variety of adjuvants well known in the art can be used in order to increase potency of the vaccine and/or modulate humoral and cellular immune responses. Suitable adjuvants include, but are not limited to, oil-in-water emulsion-containing adjuvants or water in oil adjuvants, such as mineral oil, aluminum based adjuvants, squalene/phosphate based adjuvants, Complete/Incomplete Freunds Adjuvant, cytokines and any other substances that act as immunostimulating agents to enhance the effectiveness of the vaccine.

The present application also include a method of preparing a vaccine composition comprising:
a) combining the adenovirus with an aqueous solution comprising an excipient, wherein the excipient comprises a mixture of dextran and mannitol in amounts effective to maintain at least 40% of the adenovirus activity after spray drying to provide a mixture;
b) optionally adding one or more of an adjuvant, buffer, antibiotic and/or additive to the mixture; and
c) spray drying the mixture.

In some embodiments, the method of preparing a vaccine composition further comprises reconstituting the spray dried mixture in a liquid suitable for vaccine formulations.

To measure the stability of a vaccine prepared in accordance with the present invention, the potency of the vaccine can be measured using techniques well known to those skilled in the art. For example, the generation of a cellular or humoral immune response is tested in an appropriate animal model by monitoring the generation of antibodies or immune cell responses to the vaccine. The ability of vaccine samples prepared in accordance with the method of the present invention to trigger an immune response may be compared with vaccines not subjected to the same stabilization procedures.

In some embodiments, the spray-dried adenovirus compositions of the application are used to transfer a heterologous gene or other nucleic acid sequence to target cells. Suitably, the heterologous sequence (i.e. transgene) encodes a protein or gene product which is capable of being expressed in the target cell. Suitable transgenes include desirable reporter genes, therapeutic genes and genes encoding immunogenic polypeptides (for use as vaccines). Gene therapy, an approach for treatment or prevention of diseases associated with defective gene expression, involves the insertion of a therapeutic gene into cells, followed by expression and production of the required proteins. This approach enables replacement of damaged genes or inhibition of expression of undesired genes. In some embodiments, the spray-dried adenovirus compositions of the application are used in gene therapy to transfer a therapeutic transgene or gene encoding immunogenic polypeptides to a patient.

Accordingly the present application further includes a method for delivering or transferring one or more nucleic acid sequences to target cells comprising administering an effective amount of an adenovirus composition of the application, or a pharmaceutical composition comprising an adenovirus composition of the application, to the cells. In some embodiments the nucleic acid sequence comprises one or more genes to be expressed in the cell or subject. Therefore present application also includes a method for gene therapy comprising administering an effective amount of an adenovirus composition of the application, or a pharmaceutical composition comprising an adenovirus composition of the application, to a subject in need thereof.

In some embodiments, the application includes the use of a spray dried composition of the application for delivering or transferring one or more nucleic acid sequences to target cells. In further embodiments the application includes the use of a spray dried composition of the application for gene therapy.

In some embodiments, the spray-dried adenovirus compositions of the application comprise a live adenoviral vector. By "live adenoviral vector" is meant a live adenoviral vector that is non-pathogenic or of low pathogenicity for the target species and in which has been inserted one or more genes encoding antigens that stimulate an immune response protective against other viruses or microorganisms, a reporter gene or a therapeutic protein. In particular, nucleic acid is introduced into the adenoviral vector in such a way that it is still able to replicate thereby expressing a polypeptide encoded by the inserted nucleic acid sequence and in the case of a vaccine, eliciting an immune response in the infected host animal. In one embodiment, the live adenoviral vector is an attenuated live viral vector i.e. is modified to be less virulent (disease-causing) than wildtype virus.

The basis of using recombinant adenoviruses as potential vaccines involves the incorporation of specific genes from a pathogenic organism into the genome of a nonpathogenic or attenuated adenovirus. The recombinant adenovirus can then infect specific eukaryotic cells either in vivo or in vitro, and cause them to express the recombinant protein.

In some embodiments, one or more heterologous genes of interest are inserted into the adenoviral vector. The adenoviral vectors of the application may comprise for example an adenovirus vector provided with an origin of replication, optionally a promoter for the expression of the heterologous gene(s) and optionally a regulator of the promoter. For example, adenoviruses useful in the practice of the present invention can have deletions in the EI and/or E3 and/or E4 region, or can otherwise be maximized for receiving heterologous DNA. In some embodiments, the adenoviral vector comprises a constitutive promoter adenovirus major late promoter (MLP), together with other adenoviral nucleic acid sequences operably linked to the heterologous gene(s) of interest. Tissue-specific or inducible promoters can also be used to control expression of the heterologous gene(s) of interest. In some embodiments, promoters are also be selected to be compatible with the host cell for which expression is designed.

In some embodiments, the adenoviral vector also comprises other transcriptional modulator elements such as enhancers. Enhancers are broadly defined as a cis-acting agent, which when operably linked to a promoter/gene sequence, will increase transcription of that gene sequence. Enhancers can function from positions that are much further away from a sequence of interest than other expression control elements (e.g. promoters) and may operate when positioned in either orientation relative to the sequence of interest.

In some embodiments of the application, the adenoviral vector containing one or more heterologous genes of interest is preserved according to the method of the invention before storage, or administration to a patient or host cell.

In some embodiments, nucleic acids encoding for polypeptides known to display antiviral activity, immunomodulatory molecules such as cytokines (e.g. TNF-alpha, interferons such as IL-6, and IL-2, interferons, colony stimulating factors such as GM-CSF), adjuvants and co-stimulatory and accessory molecules are comprised in the adenoviral vector of the application. Alternatively, such polypeptides are provided separately, for example in the spray dried compositions of the application or are administrated simultaneously, sequentially or separately with adenoviral vectors of the application.

In some embodiments, the spray dried compositions of the application are introduced into suitable host cells using a variety of viral techniques that are known in the art, such as for example infection with recombinant adenoviruses. In some embodiments, the introduction of the spray dried compositions of the application into suitable host cells is mediated by viral infection of a target cell.

A number of adenovirus vectors are known. Adenovirus subgroup C serotypes 2 and 5 are commonly used as vectors. The wild type adenovirus genome is approximately 35 kb of which up to 30 kb can be replaced with foreign DNA. There are four early transcriptional units (EI, E2, E3 & E4), which have regulatory functions, and a late transcript, which codes for structural proteins. Adenovirus vectors may have the EI and/or E3 gene inactivated. The missing gene(s) may then be supplied in trans either by a helper virus, plasmid or integrated into a helper cell genome. Adenovirus vectors may use an E2a temperature sensitive mutant or an E4 deletion. Minimal adenovirus vectors may contain only the inverted terminal repeats (ITRs) & a packaging sequence around the transgene, all the necessary viral genes being provided in trans by a helper virus. Suitable adenoviral vectors thus include AdHu5 vectors and simian adenovirus vectors.

In some embodiments, the spray dried compositions of the application are administered to a subject or a cell after reconstitution using a variety of known routes and techniques. For example, the spray dried compositions of the application are provided as an injectable solution, suspension or emulsion and administered via parenteral, subcutaneous, oral, epidermal, intradermal, intramuscular, interarterial, intraperitoneal, intravenous injection using a conventional needle and syringe, or using a liquid jet injection system. In some embodiments, the spray dried compositions of the application are administered topically to skin or mucosal tissue, such as nasally, intratracheally, inhalationally, intestinally, sublingually, rectally or vaginally, or provided as a finely divided spray suitable for respiratory or pulmonary administration.

The spray dried compositions of the application are administered to a subject or a cell in an amount that is compatible with the dosage formulation and that will be prophylactically and/or therapeutically effective. The administration of the spray dried compositions of the application are for either "prophylactic" or "therapeutic" purposes.

EXAMPLES

The following non-limiting examples are illustrative of the present application:

Example 1: Production, Characterization and Evaluation of Spray Dried Powders of Adenoviral Vectors Materials and Methods
Chemicals and Adenoviral Vectors Anhydrous lactose, D-(+)-trehalose dihydrate, D-mannitol, dextran ($M_r$ 40000 kDa) and L-leucine were all purchased as USP grades from Sigma-Aldrich (Ontario, Canada). Culture media was produced from α-minimum essential medium (prepared in the lab according to protocol by Life Technologies (Ontario, Canada)) with 10% fetal bovine serum and 1% streptomycin/penicillin (Invitrogen; Ontario, Canada). X-Gal stock solution was purchased from EMD Millipore (Ontario, Canada). A recombinant replication-defective human type 5 adenovirus expressing *Escheria coli* β-galactosidase (AdHu5LacZ) was produced in the vector facility of McMaster Immunology Research Centre as described previously.[34]

Spray Drying

Spray dried powders were produced using a Büchi Mini Spray Dryer B-290 (Büchi, Switzerland) with 0.7 mm spray nozzle and high performance cyclone. The setup is shown schematically in FIG. 1, consisting of the spray drying nozzle (1), the drying chamber (2), the separating cyclone (3) and the collection chamber (4). The atomizing air was dried using an in-line silica gel desiccant air dryer (McMaster-Carr; Elmhurst, Ill.) and cleaned using an Aervent® 0.2 μm filter (EMD Millipore; Billerica, Mass.). Three excipient formulations were produced: (1) L-leucine, (2) 90% lactose and 10% trehalose and (3) 67% mannitol and 33% dextran (all compositions are quoted based on percent by weight). Excipient formulations were dissolved in Milli-Q® water. The AdHu5 vector was stored in a PBS buffer; however, its addition to the excipient solution was negligible, being less than $\frac{1}{10000}^{th}$ of the spray dried volume. The concentration of the AdHu5 solution was $5\times10^7$ pfu/mL. The pH of the solution was 6.5. The composition and spray drying process parameters (Table 1) were optimized on preliminary experiments looking to achieve a high yield of non-agglomerating particles with matrices of significant amorphous content and high glass transition temperature ($T_g$), and most importantly, minimal adenoviral vector activity loss. Yield was calculated as a percentage of the mass of powder in the collection vessel compared to the input amount. All spray drying processes and powder collection were performed in a custom biosafety cabinet (Design Filtration; Ontario, Canada).

TABLE 1

Spray drying process parameters and powder recovery for each formulation.

| Parameter | L-leucine | 90% Lactose/10% Trehalose | 67% Mannitol/33% Dextran |
|---|---|---|---|
| Solid Concentration (mg/mL) | 0.3[a] | 1 | 1 |
| Spray Gas Flow (L/h) | 439.11 | 666.93[b] | 439.11 |
| Inlet Temperature (° C.) | 90 | 90 | 120[c] |
| Outlet Temperature (° C.) | 54 | 48 | 65 |
| Feed Flow Rate (mL/h) | 145.0 | 145.0 | 217.5[d] |
| Yield (%) | 81.4 | 83.1 | 84.5 |

[a]Limited solubility of L-leucine prevented concentration of 1 mg/mL.
[b]Increased spray gas flow for lactose/trehalose formulation increased powder production without any observed decrease in viral titre post-spray drying.
[c,d]Greater inlet temperature and feed flow rate increased post-spray drying viral titre.

Sample Storage

Powder samples were stored for different durations at relative humidities (RH) of <10%, 45% and >90%. Storage humidity was produced with gel desiccants and saturated salt solutions (potassium carbonate, 45% RH; potassium nitrate, >90% RH) within desiccators. The relative humidity within each compartment was confirmed before sample observation through direct measurement with a Fisher Scientific™ Traceable™ Jumbo Thermo-Humidity Meter (Fisher Scientific; Ontario, Canada), and found to vary ±3%. Liquid control samples containing only buffer and AdHu5LacZ were stored in tightly sealed vials under ambient conditions and were not stored with desiccants or saturated salts. All aging trials examining the influence of humidity were performed at 20° C. Samples and storage conditions are listed in Table 2. Sealed samples were stored in closed 2 mL Nalgene General Long-Term Storage Cryogenic Tubes (Nalgene; Ontario, Canada).

TABLE 2

Storage conditions and corresponding sample formulations.

| Storage Condition | | | |
|---|---|---|---|
| Temperature | Relative Humidity | Storage Time | Samples Stored |
| 20° C. | <10% RH | Up to 90 days (evaluated at 0, 1, 10, 45 and 90 days) | L-leucine<br>Lactose/Trehalose<br>Mannitol/Dextran |
| 20° C. | 45% RH | Up to 90 days | L-leucine<br>Lactose/Trehalose<br>Mannitol/Dextran |
| 20° C. | >90% RH | 15 days | L-leucine<br>Lactose/Trehalose<br>Mannitol/Dextran |
| 20° C. | Sealed, ambient humidity | Up to 90 days | Liquid Control |
| 37° C. | Sealed, ambient humidity | Up to 72 hours | Liquid Control<br>Mannitol/Dextran |
| 45° C. | Sealed, ambient humidity | Up to 72 hours | Liquid Control<br>Mannitol/Dextran |
| 55° C. | Sealed, ambient humidity | Up to 72 hours | Liquid Control<br>Mannitol/Dextran |

Particle Size and Morphology

Spray dried particle size and morphology were examined using a JEOL JSM-7000F scanning electron microscope (SEM) (JEOL Ltd.; Japan). Samples containing adenovirus vector were inactivated through exposure to UV light for 30 minutes prior to imaging. All samples were applied to double-sided tape and coated with a 5.0 nm layer of platinum. Micrograph images were collected at several magnifications at a working distance ranging from 10.0-10.3 mm and an electron accelerating voltage ranging from 3.0-5.0 kV. All electron microscopy was conducted at pressures less than $5.0\times10^{-4}$ Pa. SEM images were analyzed using ImageJ[35] to measure the dimensions of nodular masses found on particle surfaces.

A Malvern Mastersizer 2000G (Malvern Instruments; United Kingdom) equipped with a He—Ne laser was used to measure particle size and size distribution. Powder formulations were dispersed in anhydrous ethanol at concentrations of 0.3 mg/mL, 1.0 mg/mL and 1.0 mg/mL for L-leucine, lactose/trehalose and mannitol/dextran formulations, respectively. Mean powder particle size was determined as the average diameter (n=3), and represented as Feret diameters as powders are not entirely spherical. Powder size span was calculated using Equation 1, where D(0.9) represents the diameter greater than 90% of measured particles, D(0.1) represents the diameter greater than 10% of measured particles and D(0.5) represents the median diameter.

$$\text{Span} = \frac{[D(0.9) - D(0.1)]}{D(0.5)} \quad (1)$$

X-Ray Photoelectron Spectroscopy

Surface elemental analysis was performed using a Physical Electronics (PHI) Quantera II X-ray photo electron spectrometer (Physical Electronics; Chanhassen, Mich.). Samples containing adenoviral vectors were inactivated through exposure to UV light for 30 minutes. X-rays were generated using an Al source and focused with a quartz crystal monochromator. A monochromatic Al K-α X-ray (1486.7 eV) source was operated at 50 W 15 kV with a spot size of 200 μm and at pressures less than $2.67\times10^{-6}$ Pa. Each recorded measurement was a survey spectra average of five sample scans. Data manipulation and analysis was performed using PHI MultiPak software (Physical Electronics; Chanhassen, Mich.).

Argon etching was accomplished using a 500V beam of Ar to bombard the surface of each specimen. Approximately 100 nm was removed from each sample using etch rates based off of computer simulated Monte Carlo calculations.[36]

Moisture Uptake of Spray Dried Particles

For analysis of moisture content, aged spray dried powders without the adenoviral vector were dissolved in formamide and injected into a Mettler Toledo DL39 Coulometric Karl Fischer Titrator (Mettler Toledo; Columbus, Ohio). The corresponding water content was determined using Equation 2:

$$\text{Water content [ppm]} = x \cdot \frac{f2 + f3}{f3} - \frac{f1 \cdot f2}{f3} \quad (2)$$

where x was the measured water content of the sample after Karl Fischer titration (ppm), and f1 was the water content of the solvent used (ppm). Water content of the formamide solvent was measured by adding formamide without dissolved solids to the Karl Fischer titrator. f2 was the measured mass of solvent (g) and f3 represents the mass of dissolved sample (g).

Thermal Properties of the Spray Dried Particles Thermograms for the three excipient formulations (without adenoviral vector) were measured using a differential scanning calorimeter (DSC). Samples of 3-10 mg were weighed into hermetically sealed aluminum pans for analysis in a Q200 Differential Scanning calorimeter (TA Instruments; New Castle, Del.). The procedure for measurement involved first equilibrating the sample at 4° C. Sample was heated to 300° C. at a ramp rate of 10° C./min under a nitrogen purge gas flowing at 50 mL/min. The heating rate was established from a previous study characterizing lactose and trehalose samples.[37] Thermal events were recorded from a single heating ramp to avoid dehydration of the sample.

Crystallinity of Spray Dried Particles

The excipient formulations (without adenoviral vector) were characterized by powder X-ray diffraction (XRD) on a Bruker D8 Discover with DAVINCI.DESIGN difractometer (Bruker; Billerica, Mass.) using a Cobalt Sealed Tube Source ($\lambda_{avg}$=1.79026 Å, 2Θ=5-70°). Small sample quantities were mounted on a silica base for examination. A blank silica sample signal was subtracted from each measured data set using GADDS software (Bruker; Billerica, Mass.), and the resulting signal intensity was integrated into a crystallographic figure through the use of DIFFRAC.EVA software (Bruker; Billerica, Mass.). Crystalline content was determined using TOPAS software (Bruker; Billerica, Mass.).

In Vitro Testing of Spray Dried Particles

Culturing of A549 Cells

A549 lung epithelial cells were thawed from liquid nitrogen and cultured in T150 culture flasks using culture media. All cell culturing was completed in a humidified Forma Series II Water Jacketed $CO_2$ Incubator (Thermo Scientific Corporation; Waltham, Mass.) at 37.0° C. and 5.0% $CO_2$. When cells were 80-90% confluent, they were split to a new T150 flask and/or plated in a 96-well plate for in vitro testing.

Excipient Toxicity

Approximately 10 mg of each spray dried formulation (without adenoviral vector) was dissolved within 100 μL of culture media and added to A549 epithelial cells plated within a 96-well plate through the use of a Gilson micropipette (Gilson; Middleton, Wis.). Control samples contained only 100 μL of culture media. Cells were left to incubate for 24 hours. After incubation, A549 cells were trypsinized and tested for viability through use of a trypan blue solution (Life Technologies; Ontario, Canada). Cell suspensions were mounted on a Bright-Line™ hemacytometer (Reichert; Buffalo, N.Y.) and the number of viable and nonviable cells were counted. Results are reported as percentage of viable cells measured and error bars represent the standard deviation (n=3).

Spray Dried Formulation Viral Infectivity

The retained viral activity or infectivity of AdHu5LacZ vector after spray drying and storage was determined by infecting plated A549 cells with approximately 3 mg of spray dried powder (input concentration of $7.56 \times 10^6$ $TCID_{50}$/mg) reconstituted in culture media right before testing. The dosages were small in volume, as up to 100 mg of powder could be contained within a 2 mL Nalgene General Long-Term Storage Cryogenic Tube. Furthermore, each 3 mg dosage could be reconstituted in as little as 60 μL of PBS. These low powder dosage amounts indicated low space constraints for storage and transport. Eight-fold serial volume dilutions were created from each reconstituted sample, ranging from a dilution of $10^{-1}$ to a dilution of $10^{-8}$ or ranging from a dilution of $10^0$ to a dilution of $10^{-7}$. Cells were incubated with AdHu5LacZ for 24 hour, and then fixed using a 0.2% glutaraldehyde (Sigma Aldrich; Ontario, Canada)/0.8% formaldehyde (Sigma Aldrich; Ontario, Canada) solution in phosphate buffered saline (% v/v) for less than five minutes. After removal of fixative, viral infection was detected as X-gal color reaction indicative of the cells transduced by infectious AdHu5LacZ viral particles present in the dried powder using the substrate 5-bromo-4-chloro-3-indoyl β-(D)-galactoside (X-gal). The number of cells positive for color reaction was determined using an Axiovert 25 inverted light microscope (Zeiss; Germany). Median tissue culture infectious dose ($TCID_{50}$) was then calculated using the Reed-Muench method as detailed within the literature.[38] Results are reported as loss of viral activity (log $TCID_{50}$/mg) and error bars are calculated as the standard deviation (n=3).

Data Analysis

Where applicable, results were statistically analyzed using the statistical package R (R Foundation for Statistical Computing; Austria). Results were considered statistically significant for $p \leq 0.05$.

Results and Discussion

Characterization of Spray Dried Powders without Adenoviral Vector

Size and Morphology

Figure 2:
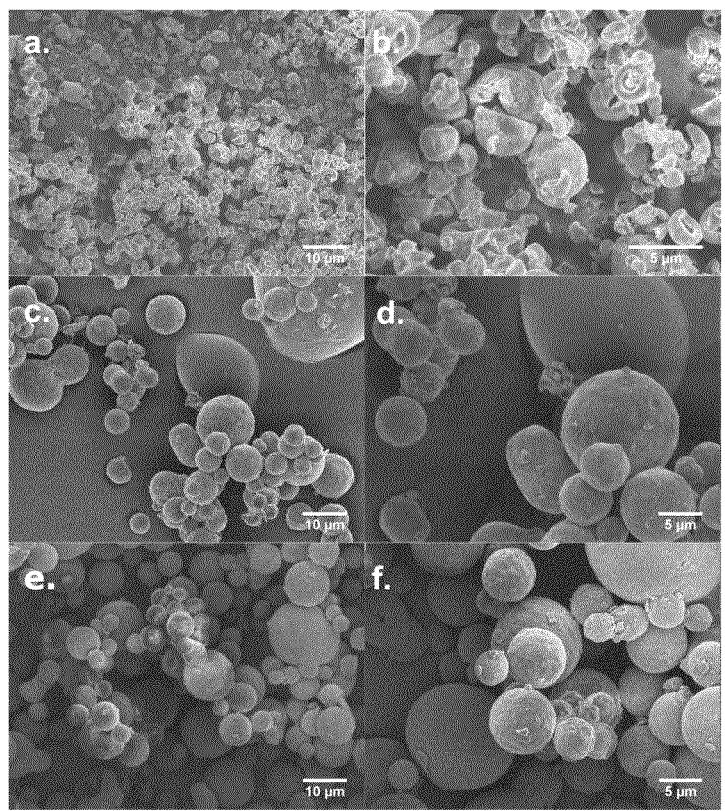
FIG. 2 shows spray dried particles imaged by scanning electron microscopy composed of L-leucine (a,b), lactose/trehalose (c,d) and mannitol/dextran (e,f). These spray dried formulations do not contain adenoviral vector.

The spray dried powder formulations were imaged by SEM at varying magnifications to evaluate size and morphology, as shown in FIG. 2. L-leucine particles were generally less than 10 μm in Feret diameter (FIGS. 2a and 2b), with an average of 8.80 μm (Table 3). These particles had a "collapsed sphere" morphology as a result of the hydrophobic isobutyl side chain on L-leucine which enhanced its surface activity,[39] causing reduced diffusion within the drying droplet. Particle precipitation that is greatly limited by excipient diffusion throughout the drying process has a high Peclet number. In these cases, evaporation occurs more quickly than diffusion, and thus diffusion of the excipient is the limiting factor.[40] This results in an early onset of particle precipitation and the formation of hollow spheres that are prone to collapse, as seen with the L-leucine formulation. Both lactose/trehalose (FIGS. 2c and 2d) and mannitol/dextran (FIGS. 2e and 2f) formulations showed spherical morphologies when spray dried. These latter cases are indicative of systems with a lower Peclet number due to their enhanced solubility and reduced surface activity.[41] Average particle Feret diameter for the lactose/trehalose and mannitol/dextran powders were 32.2 μm and 7.92 μm, respectively (Table 3). The larger average particle size for the lactose/trehalose formulation can be attributed to a greater amount of agglomeration between developed particles (notable by the bridging outlined in FIGS. 2c and 2d). The span listed in Table 3, is indicating a wide particle size distribution for all spray dried formulations. Overall, particle sizes were larger than might be expected from the initial solution concentrations. This is a result of the spray drying process, as completely condensed particles are unlikely to form, as shown in FIG. 2b.

TABLE 3

Average spray dried particle size and span (calculated by equation 1), measured by Mastersizer, for the three formulations tested.

| Formulation | $D_{50}$ (μm) | Span |
|---|---|---|
| L-leucine | 8.80 | 2.05 |
| Lactose/Trehalose | 32.2 | 1.73 |
| Mannitol/Dextran | 7.92 | 1.61 |

Moisture Uptake

Figure 3:
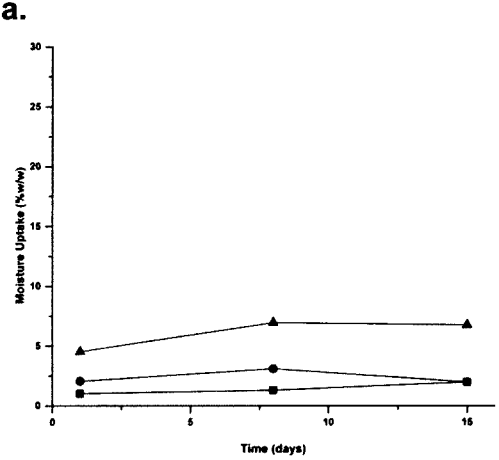
FIG. 3 shows moisture uptake (wt. %) of L-leucine (a), lactose/trehalose (b) and mannitol/dextran (c) formulations after storage for up to two weeks at 20° C. and relative humidities of <10% (■), 45% (●) and >90% (▲).
Figure 3:
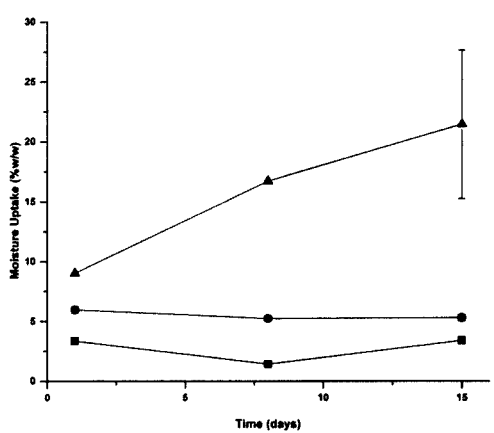
Figure 3:
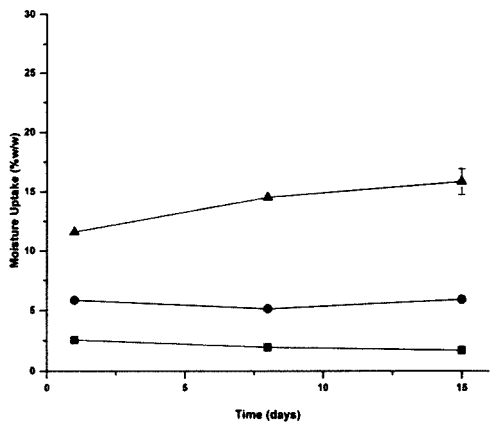

The measured water content after storage under different humidity conditions is plotted in FIG. 3 for the three spray dried formulations. For the 15 day evaluation, the least hygroscopic spray dried powder was produced with the L-leucine formulation. Total moisture content for L-leucine (measured as percent weight of the total) was 0.98%, 1.98% and 6.76% under controlled relative humidity conditions of <10, 45 and >90% RH, respectively. In comparison, the lactose/trehalose formulation absorbed significant amounts of water, measured as 2.54%, 4.21% and 17.08% for <10, 45, and >90% RH, respectively. A similar amount of moisture uptake was determined for the mannitol/dextran formulation; at <10, 45, and >90% RH, the respective 15 day measurements were 1.72%, 5.89% and 15.05%.

Many pharmaceutically relevant excipients have hydrogen bonding potential, allowing for the binding of water from their surrounding environment.[42] The absorption of water within solid dispersions is generally deleterious, destabilizing their physical structure by depressing the $T_g$ and inducing changes within the crystalline structure. As a result, minimal moisture uptake is optimal for the dispersed active ingredient to remain immobilized for as long as possible.[18,43] The low water sorption capacity of L-leucine particles is due to the high crystalline content. Furthermore, the spray drying process orients the hydrophobic isobutyl groups towards the air phase and hydrophilic amide groups towards the water phase during evaporation.[44,45] Both lactose and trehalose are considered to be highly hygroscopic materials and hence, it was not unexpected that the spray dried particles from these ingredients similarly showed high moisture uptake in the experiments. Mannitol is typically crystalline and non-hygroscopic,[46] yet the inclusion of dextran produced spray dried particles with high moisture sensitivity.

All spray dried powders showed no significant change in moisture content after day 1 when stored at 45% RH or less. In comparison, when stored at >90% RH the powders continued to uptake water and showed no evidence of approaching an equilibrium condition within the tested 15 day period. The spray dried powders stored at >90% RH proved too difficult to preserve in their current state for the detailed characterizations. These powders agglomerated into large masses and were very sticky, proving to be difficult to work with and unsuitable for AdHu5 stabilization.

Crystallinity

Figure 4:
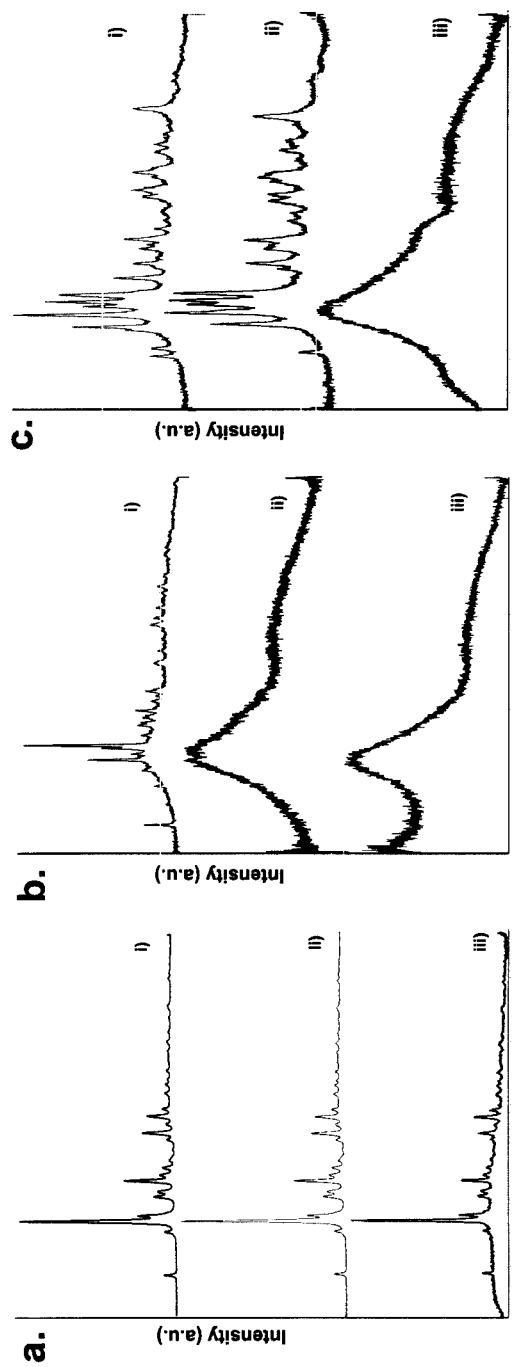
FIG. 4 shows X-ray diffraction peak crystal intensities (arbitrary units) measured across a range of x-ray incidence angles for L-leucine (a), lactose/trehalose (b) and mannitol/dextran (c) formulations. Storage conditions are immediately post spray drying (i), two weeks storage at 20° C. and <10% RH (ii) and two weeks storage at 20° C. and 45% RH (iii).

The three spray dried powders were analyzed by X-ray diffraction as shown in FIG. 4; crystal structure differences were attributed to the different chemical composition of each formulation. Measured crystalline content is shown in Table 4 for each formulation immediately after spray drying. The crystallinity for L-leucine was very high, as the particle was mostly crystallized. Both lactose/trehalose and mannitol/dextran formulations were measured to be semicrystalline. Crystallinity of each formulation was determined using x-ray diffractograms, as it has been previously published that measuring crystallinity of specific materials from differential scanning calorimetry thermograms can lead to erroneous results.[47]

TABLE 4

Measured crystallinity for all formulations immediately after spray drying.

| Formulation | Measured Crystallinity (%) |
| --- | --- |
| L-leucine | >97% |
| Lactose/Trehalose | 56% |
| Mannitol/Dextran | 44% |

FIG. 4a displays diffraction patterns for the crystalline structure of spray dried L-leucine. L-leucine has a propensity to crystallize,[48] and the sharp peaks in the diffractogram indicate a highly regular crystalline structure was immediately present after spray drying as well as after two weeks of storage at 20° C. and <10% RH. Under conditions of 20° C. and 45% RH, a small amount of peak broadening was observed for L-leucine. This broadening corresponds with a marginal increase in water content at these conditions, suggesting absorbed water may have partially dissolved and/or disrupted the L-leucine crystal structure.

The diffraction patterns in FIG. 4b for the lactose/trehalose formulation displayed crystalline α-lactose monohydrate peaks as well as a large amorphous peak, when powders were tested immediately after spray drying. The significant amorphous content shown was expected having been previously reported for spray dried lactose[50] and furthermore, blends of lactose and trehalose are known to inhibit crystallization in the complementary component.[51] After storage at 20° C. for two weeks, the crystalline regions were less apparent by XRD, even at low humidity. The work of other authors has demonstrated that the onset of crystallization for lactose and trehalose blends occur at 65.6% RH,[51] thus storage of these powders at 45% RH and <10% RH does not allow sufficient moisture for a thermodynamically equilibrated crystal structure to emerge. The broadening of diffraction peaks at these conditions coincided with a decrease in crystallinity similar to what happens when water is lost from a crystalline trehalose structure, resulting in a mostly amorphous material.[52] This effect of dehydration on crystal structures has been previously reported under mild conditions for both raffinose- and trehalose-based systems.[53,54] This process should be anticipated more so in spray dried systems, where the particle is trapped in an unfavourable state as a result of fast drying.[55] The broad peaks in FIG. 4b (ii, iii) were attributed to the small-sized crystal domains detected by DSC and notably identified by other authors as a crystal structure is reverted to a mostly vitrified glass.[53,56]

FIG. 4c shows the diffraction patterns for the mannitol/dextran formulation. As expected based on other studies,[57] dextran exhibited no crystalline peaks in XRD. The crystalline peaks of mannitol were shifted in the presence of dextran, though most closely resembled the α-polymorphic form.[58] After two week storage at 20° C. and <10% RH, no change in crystallinity was observed. When stored at 20° C. and 45% RH, a single broad mixed-mode peak was found as a result of the significant water uptake shown in FIG. 3. Both α- and β-polymorphic forms of pure mannitol are reportedly structurally stable in the presence of high RH for several weeks, though under those condition, crystallinity is gradually decreased.[58] The relatively hygroscopic nature of dextran included in the blend increased the sensitivity of mannitol crystals to water.[59]

Overall, the presence of moisture is detrimental to the structural stability of the matrix as seen by changes in crystal structure for all three excipient formulations. These changes in crystal structure are indicative of movements on the molecular scale, which correspond to activity loss in spray dried particles containing adenoviral vectors, as discussed further below.

Thermal Properties

The thermal transitions of spray dried particles from each of the three formulations were analyzed by DSC. The glass transition temperature and peak fusion/sublimation temperature ($T_m$) are given in Table 5. Spray dried L-leucine particles had sufficiently high crystallinity that the glass transition temperature could not be detected. An endothermic peak at 247° C. corresponded to the sublimation of L-leucine.[60] Both lactose/trehalose and mannitol/dextran formulations exhibited relatively high $T_g$ values immediately after spray drying, measured at 115° C. and 130° C., respectively. The $T_m$ of 214° C. for lactose/trehalose indicated a depressed melting point that was 8° C. below the α-form of crystalline lactose[61]. The $T_m$ of mannitol/dextran was 162° C., lower than the 170° C. reported for pure mannitol.[58]

After storage for two weeks at 20° C. and under dry conditions (<10% RH), the lactose/trehalose and mannitol/dextran powder $T_g$ did not change noticeably, as shown in Table 4. However, after storage for two weeks at 20° C. and intermediate humidity conditions (45% RH), the $T_g$ for lactose/trehalose and mannitol/dextran decreased significantly to 15° C. and 45° C. respectively. The decrease in measured $T_g$ is caused by the plasticizing effect of absorbed water.[43]

The $T_m$ and especially $T_g$ were parameters useful in determining matrix stability in terms of immobility. Simply stated, higher $T_g$ and $T_m$ were optimal due to the higher ambient temperatures to induce destabilizing molecular movement. However, if $T_g$ and $T_m$ alone were used to predict viral vector stability then L-leucine would appear to be best, followed by lactose/trehalose and mannitol/dextran which are similar in thermal properties, however, this is not the trend observed for viral activity emphasizing the importance of water uptake, degree of crystallinity, particle morphology and in vitro assays to properly predict excipient performance.

TABLE 5

Measured glass transition temperature ($T_g$) and fusion/sublimation temperature ($T_m$) for three formulations.

| Formulation | Day 0 | | Day 15: 20° C./0% RH | | Day 15: 20° C./45% RH | |
|---|---|---|---|---|---|---|
| | $T_g$ | $T_m$ | $T_g$ | $T_m$ | $T_g$ | $T_m$ |
| L-leucine | —[a] | 246.8° C. | —[a] | 252.5° C. | —[a] | 247.0° C. |
| Lactose/Trehalose | 114.8° C. | 213.8° C. | 113.8° C. | 213.7° C. | 17.6° C. | 208.1° C. |
| Mannitol/Dextran | 127.3° C. | 162.4° C. | 127.3° C. | 162.8° C. | 45.9° C. | 153.5° C. |

[a]L-leucine particles exhibited no detectable $T_g$.

Excipient Cytotoxicity

To ensure accurate viral infection measurements, the base spray dried formulations without adenoviral vector were tested for their relative toxicity to the plated A549 cells at a dosage level that was three times higher than used for the particles containing adenovirus. Cell viability corresponding to each formulation is shown in Table 6. No cytotoxicity was observed for the three formulations based on the absence of any significant differences in cell viability between the formulations and the control (cell culture media).

TABLE 6

Measured A549 cell viability (%) after 24 hour incubation with each formulation (mean ± SD, n = 3).

| Formulation | Measured Viable Cells (%) |
|---|---|
| L-leucine | 98 ± 3 |
| Lactose/Trehalose | 97 ± 1 |

TABLE 6-continued

Measured A549 cell viability (%) after 24 hour incubation with each formulation (mean ± SD, n = 3).

| Formulation | Measured Viable Cells (%) |
|---|---|
| Mannitol/Dextran | 98 ± 2 |
| Control | 96 ± 2 |

Figure 5:
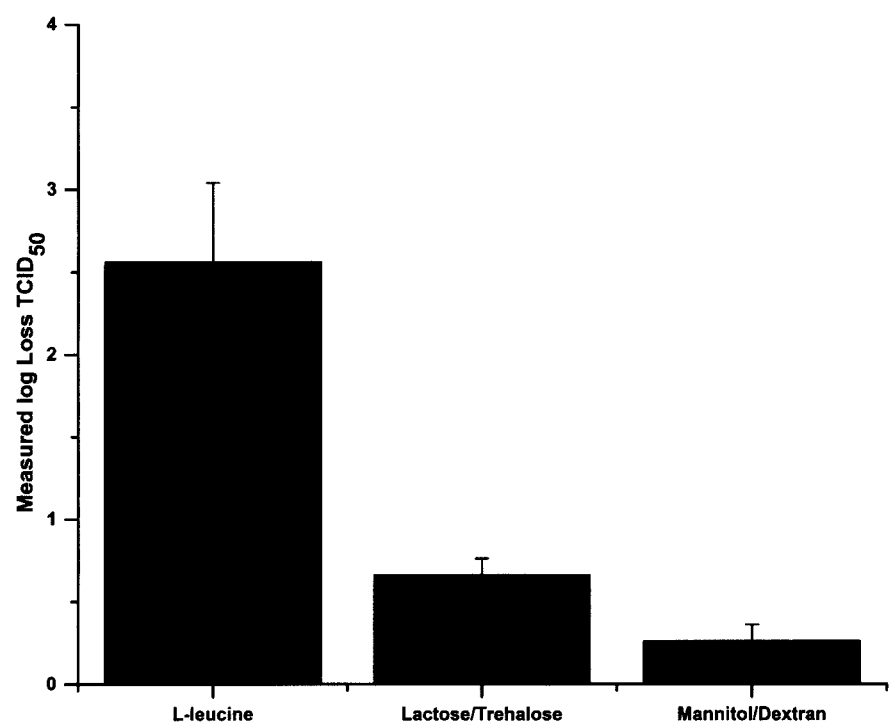
FIG. 5 shows measured loss of AdHu5 infectivity for L-leucine, lactose/trehalose and mannitol/dextran, formulations after spray drying.

Evaluation of Spray Dried Particles Containing Adenoviral Vector
Retained Viral Activity after Spray Drying Spray dried powders containing human type 5 adenoviral vector expressing *Escheria coli* β-galactosidase (AdHu5LacZ) were prepared and were indistinguishable in appearance from the powders without the viral vector. The high temperatures and shear rates experienced during the spray drying process could presumably lead to some loss in viral infectivity and as such, the vector activity for each formulation was tested immediately after spray drying. As shown in FIG. 5, while the L-leucine formulation resulted in a relatively large loss in activity (2.6±0.5 log), the lactose/trehalose and mannitol/dextran formulations exhibited excellent retention of adenoviral vector infectivity with less than 1.0 log loss. Within the literature, activity loss post-spray drying can be reportedly greater than 3.0 log, though this is highly variable depending on the labile material used and the method of measuring activity.[25,26] The activity loss for spray dried mannitol/dextran with AdHu5 particles was the smallest within this report, being only 0.3±0.1 log. For all three formulations, the collected powder recovery after spray drying was greater than 80% (Table 1) which was important because it implied an efficient processing method where there was no significant loss of valuable biological material, such as the AdHu5LacZ vector tested here.

Figure 6:
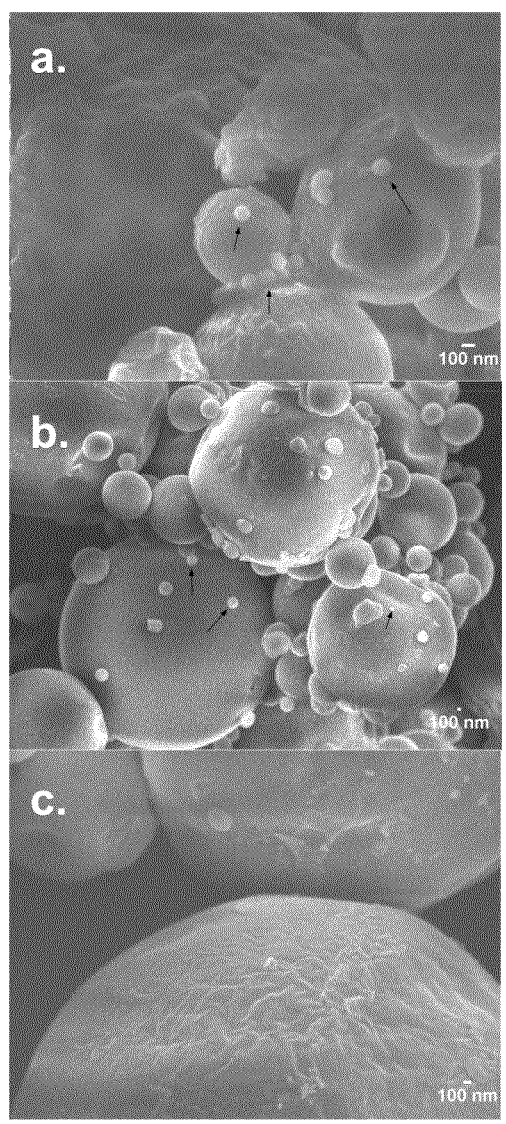
FIG. 6 shows SEM micrographs of spray dried adenoviral vector formulations: L-leucine (a), lactose/trehalose (b) and mannitol/dextran (c). Proposed AdHu5 nodules present on the particle surface are indicated by black arrows.

SEM micrographs of spray dried particles containing the adenoviral vector are shown in FIG. 6, demonstrating differences in the extent to which the virus was incorporated within each matrix. While not wishing to be limited by theory, the large AdHu5 activity loss observed for L-leucine particles may be due to phase separation of the excipient and the adenoviral vector. Nodules were observed at the powder surface (highlighted by black arrows in FIG. 6a) which may imply that some AdHu5 is not fully encapsulated. This is in contrast to the L-leucine particles spray dried without AdHu5 shown in FIGS. 2a and 2b. These nodules were measured to be 99±8 nm in diameter which is similar to the reported AdHu5 vector diameter of 70-100 nm.[62] Separation could occur due to the high Peclet conditions of L-leucine during spray drying and the "expelling" nature of forming crystals. Due to the low solubility of L-leucine molecules, supersaturation at the droplet surface is thought to occur early in the drying process.[55] The diffusion coefficient for this phase-separated supersaturated domain is magnitudes smaller than that of lactose, trehalose, mannitol or dextran. The result is a Peclet number much greater than 1. Furthermore, a crystalline material is unlikely to form stabilizing bonds with any other material, as it is instead more favourable to continue the crystal structure without faults.[63] While not wishing to be limited by theory, the coupling of high Peclet conditions and poor labile material stabilization in a crystalline product may explain the greater loss of AdHu5 activity after spray drying with L-leucine. In FIG. 6b, the addition of the adenoviral vector to the spray dried lactose/trehalose formulation also resulted in nodules on the particle surface, although these nodules were 330±90 nm in diameter, much larger than the AdHu5 vector. These nodules, which were not seen in FIG. 2 for particles without AdHu5LacZ, could indicate surface localization of the adenoviral vector, now better encapsulated within a layer of excipient than found with L-leucine. This interpretation of the morphology appears consistent with the infectivity data since the viral vector would have been better isolated from the environment than within L-leucine particles yet not quite so well shielded as in mannitol/dextran. No nodules were visible on the mannitol/dextran particles containing AdHu5 (FIG. 6c) indicating complete incorporation.

To improve confidence as to the source of the nodule morphology, the surface characterization technique XPS was used to detect nitrogen as a marker for AdHu5LacZ because this element is not present in lactose, trehalose, mannitol or dextran. Testing by this technique was not done with L-leucine since no element could be identified as a unique marker in this case. The adenoviral vector was unlikely to be solely localized in the nodules but the presence of the nodules suggested closer proximity to the particle surface if they did in fact contain AdHu5LacZ and hence XPS should have an increased probability detecting the nitrogen should this hypothesis prove valid. Nitrogen was detected once out of three tests at the surface of the lactose/trehalose particles and once again out of five tests after argon etching away a surface layer of 100 nm in thickness. The same number of tests were conducted with mannitol/dextran particles, with nitrogen never being detected. The surface elemental composition for selected tests of both lactose/trehalose and mannitol/dextran powders is shown in Table 7. As an approximate calculation, AdHu5LacZ is estimated to be composed of 20% nitrogen by weight,[64,65] and thus for XPS with a detection threshold of 0.5 wt. %, the surface area coverage of AdHu5LacZ to excipient must be over 2.5% for a signal that is readily distinguishable from instrumental noise. This level of surface coverage is possible but the distribution of components is not expected to be perfectly uniform over different areas sampled by the XPS beam. Thus in some XPS spectra, nitrogen could be detected, whereas in others it was absent. The description of the nodules as containing AdHu5LacZ seems compelling based on these SEM and XPS results, and without being limited by theory, provides a reasonable explanation, in part, for the differences in thermal stability noted between these three excipient formulations.

TABLE 7

Elemental composition by XPS for lactose/trehalose and mannitol/dextran samples (n = 8) before and after argon etching 100 nm into the sample.

| Formulation | % Composition Pre-etch | | | % Composition Post-etch | | |
|---|---|---|---|---|---|---|
| | C | O | N | C | O | N |
| Lactose/Trehalose | 51.8 | 48.2 | 0.0 | 52.0 | 47.8 | 0.7[a] |
| Mannitol/Dextran | 57.6 | 42.4 | 0.0 | 58.9 | 41.1 | 0.0 |

[a]Nitrogen content was present in two lactose/trehalose samples of eight.

To highlight the fact that the presence of nodules indicating poorly incorporated AdHu5 can only be part of the explanation for the differences in thermal stability seen in the tests, the measured viral infectivity loss of only 0.7±0.1 log for the lactose/trehalose formulation needed to be reiterated. While not wishing to be limited by theory, the greater activity retained with this formulation compared to L-leucine may be attributed to the exceptional stabilizing profile of trehalose with other bioactive compounds.[66] Trehalose has previously been proposed to be a good "water replacing" molecule throughout the drying process as it is able to replace stabilizing hydrogen bonds between water molecules and viral protein structures.[67] Thus, although some segregation between adenoviral vector and formulation excipients may be occurring, trehalose provides good stabilization throughout the spray drying process. In addition, total vector loss from segregation between the adenoviral vector and excipient matrix was not necessarily properly observed through SEM. It is highly probable that some AdHu5 that failed to be incorporated within the matrix would become detached from the particle at some point. The total encapsulation of AdHu5LacZ in mannitol/dextran powders is correlated to the low activity loss after spray drying. As described previously, particle formation is affected by diffusion of the excipient components in aqueous solution during spray drying; dextran diffusion is heavily restricted compared to lactose and trehalose, which are much smaller sugars.[68] Thus precipitation at the droplet surface likely begins with dextran, providing less opportunity for adenovirus segregation to the outer particle surface. These results highlight that the chemical nature of the excipients plays a role in their ability to trap and stabilize AdHu5 vector and that morphological inspection of spray dried particles offers further insight into the ability of some formulations to maintain viral infectivity better than others.

Viral Infectivity After Storage at 20° C. and Differing Humidity

Figure 7:
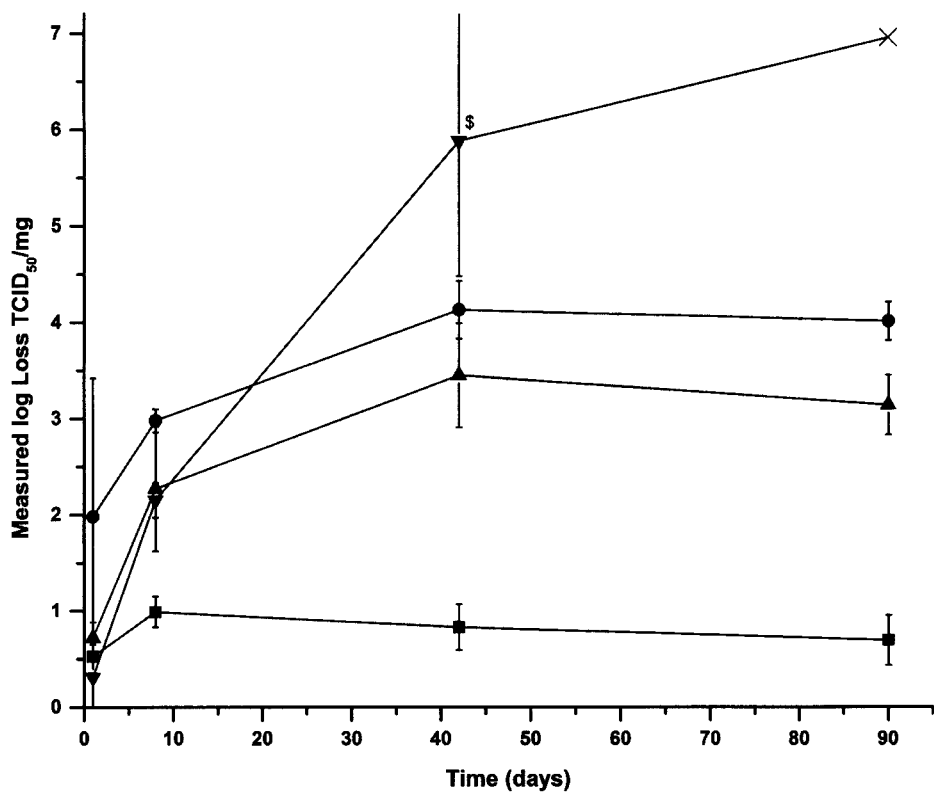
FIG. 7 shows measured log loss of AdHu5 vector infectivity after storage up to 90 days at 20° C. and <10% RH for liquid control (▼), L-leucine (●), lactose/trehalose (▲) and mannitol/dextran (ζ), formulations. Three repeat samples were stored for each formulation and $ denotes viral activity below the detection limit for one repeat, $$ denotes viral activity below the detection limit for two repeats, and 'x' denotes viral activity below the detection limit for all repeats.

FIG. 7 shows the resulting adenoviral vector titre loss through storage at 20° C. at <10% RH for each spray dried formulation up to 90 days. For the liquid control (AdHu5LacZ in buffer), significant AdHu5 vector infectivity was lost after 42 days at 20° C. and there was no measurable activity after 90 days. This relatively rapid loss of adenoviral vector activity corresponds to previously reported data[13] and further highlights the need for vector stabilization at temperatures above the normal cold chain storage conditions of −80° C. All excipient formulations outperformed the liquid control. However, the mannitol/dextran formulation was able to retain higher viral activity than the other formulations at day 90 for the low humidity condition (p<0.01). The measured AdHu5 titre loss at day 90 was 0.7±0.3 log with mannitol/dextran-formulated vector, only slightly higher than the 0.3±0.1 log measured directly after spray drying. Adenoviral vectors stabilized within lactose/trehalose did not maintain the same degree of function as those stabilized within mannitol/dextran. After 90 days, the measured loss of infectivity for these samples was measured at 3.1±0.3 log. Similarly, L-leucine exhibited poor excipient stability as the measured activity loss on day 90 was 4.0±0.2 log. For all formulations, the vector activity loss was greatest within the first two weeks. This was likely due to the greater amount of molecular movements within the particle as it transitioned to an equilibrated state post-spray drying.

Figure 8:
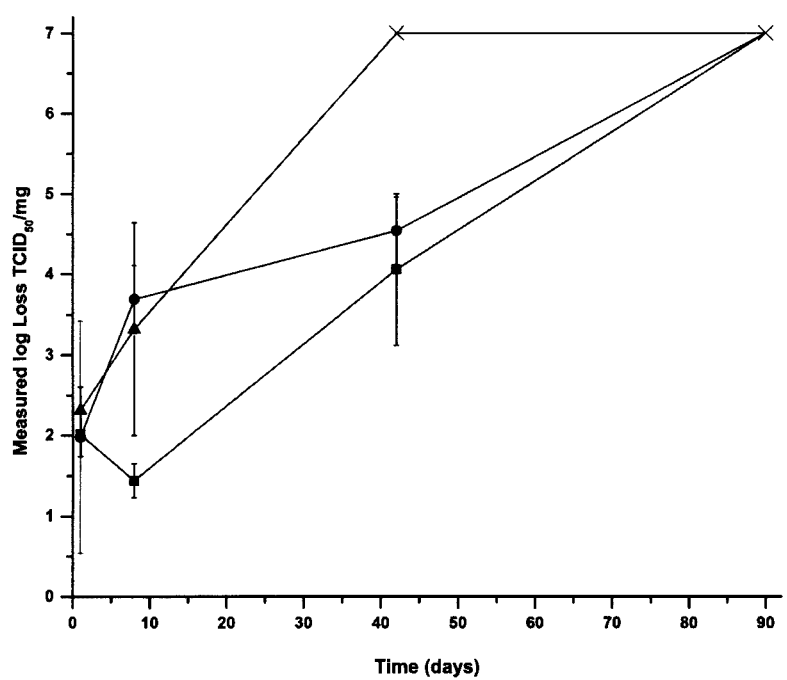
FIG. 8 shows measured log loss of AdHu5 vector infectivity after storage up to 90 days at 20° C. and 45% RH for L-leucine (●), lactose/trehalose (▲) and mannitol/dextran (■) formulations. Three repeat samples were stored for each formulation and 'x' denotes viral activity below the detection limit for all repeats.
Figure 9:
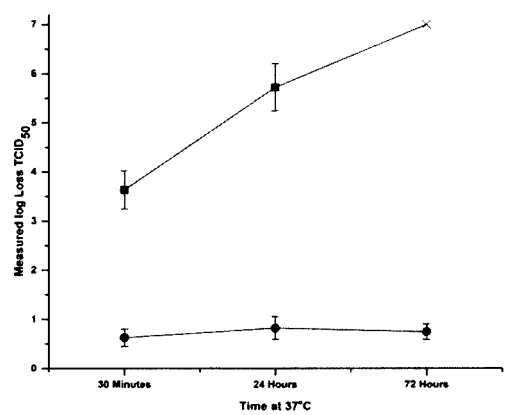
FIG. 9 shows measured AdHu5 infectivity loss for both control (■) and mannitol/dextran formulation (●) at a storage of 37° C. (a), 45° C. (b) and 55° C. (c) for up to three days. Three repeat samples were stored for each formulation and 'x' denotes viral activity below the detection limit for all repeats.
Figure 9:
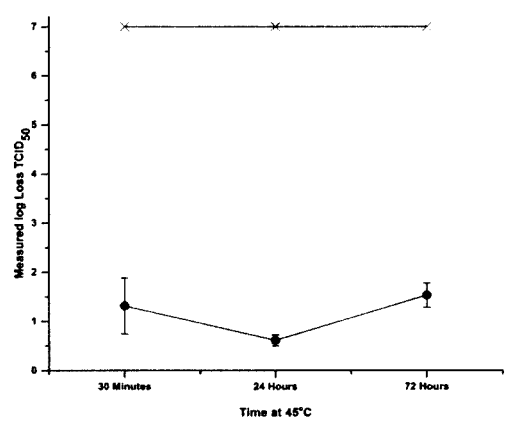
Figure 9:
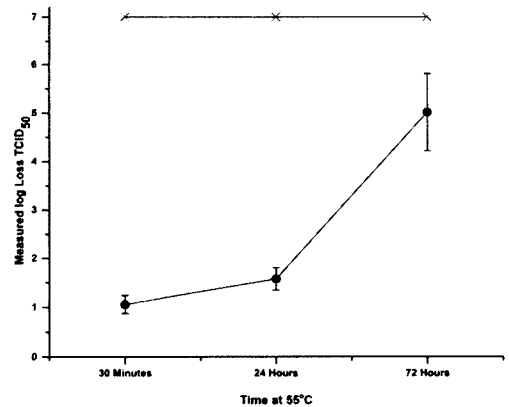
Figure 10:
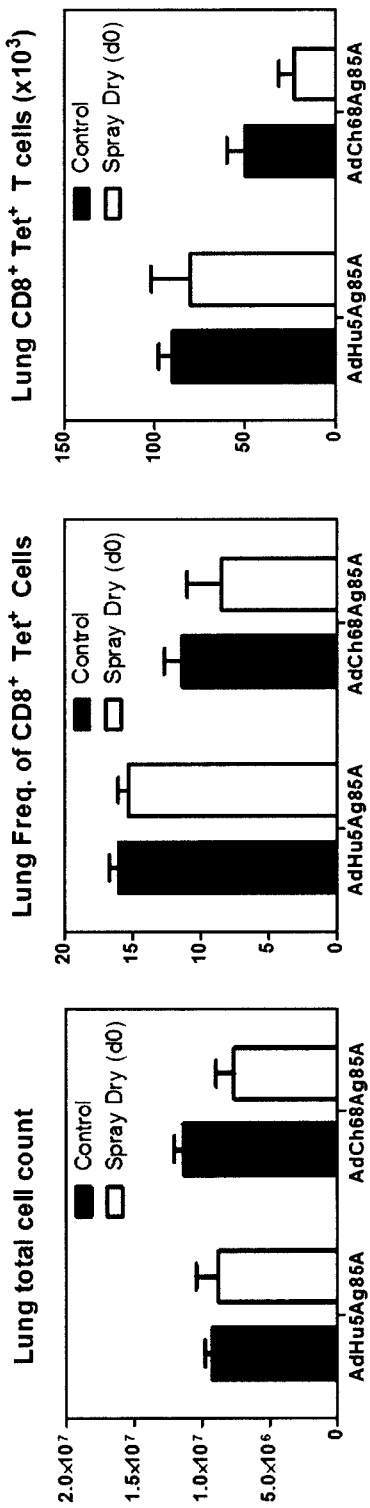
FIG. 10 shows viral infectivity of AdHu5Ag85A and AdCh68Ag85A in the lung of mice, comparing administration via a PBS solution and a reconstituted exemplary composition of the application immediately after preparation of the formulations.
Figure 11:
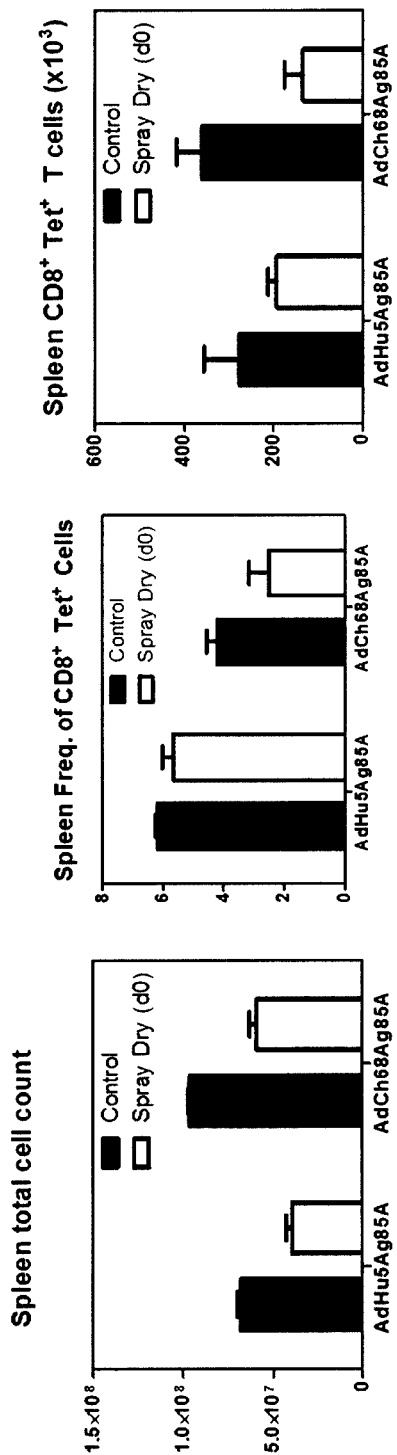
FIG. 11 shows viral infectivity of AdHu5Ag85A and AdCh68Ag85A in the spleen of mice, comparing administration via a PBS solution and a reconstituted exemplary composition of the application immediately after preparation of the formulations.
Figure 12:
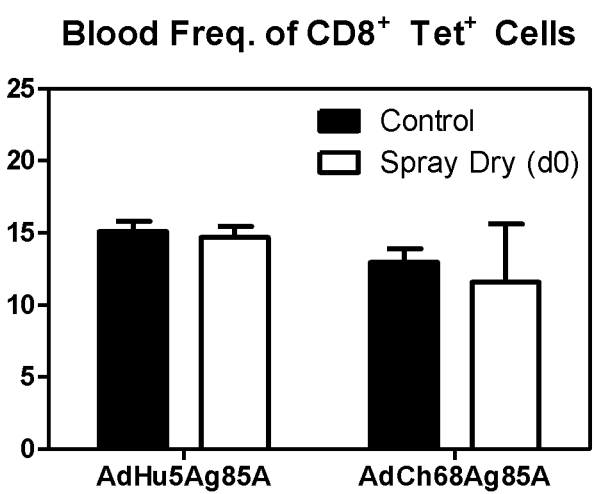
FIG. 12 shows viral infectivity of AdHu5Ag85A and AdCh68Ag85A in the blood of mice, comparing administration via a PBS solution and a reconstituted exemplary composition of the application immediately after preparation of the formulations.
Figure 13:
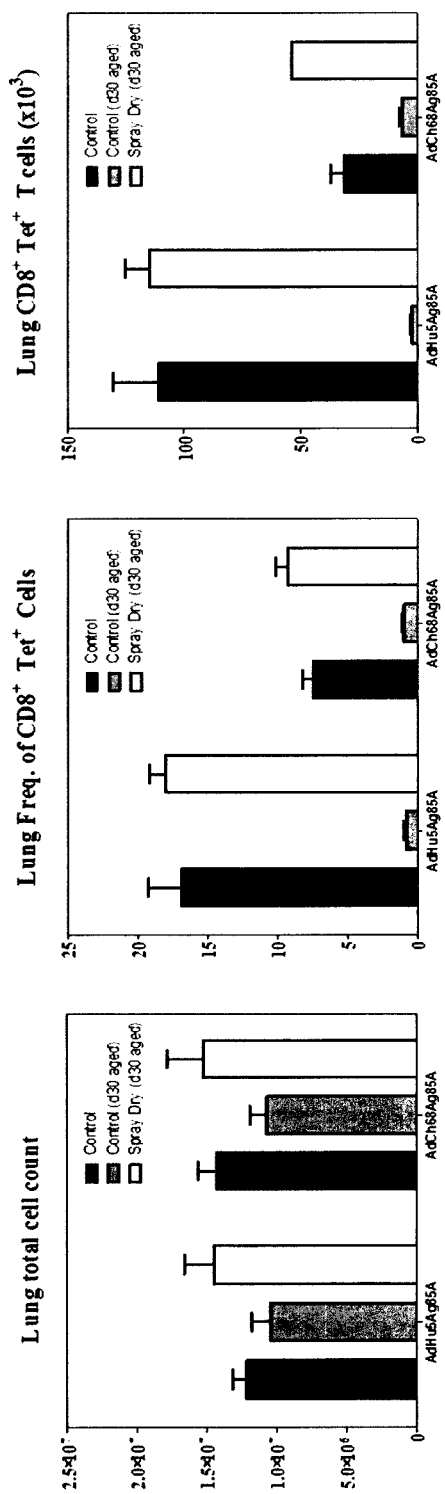
FIG. 13 shows viral infectivity of AdHu5Ag85A and AdCh68Ag85A in the lung of mice, comparing administration via a PBS solution and a reconstituted exemplary composition of the application 30 days after preparation of the formulations.
Figure 14:
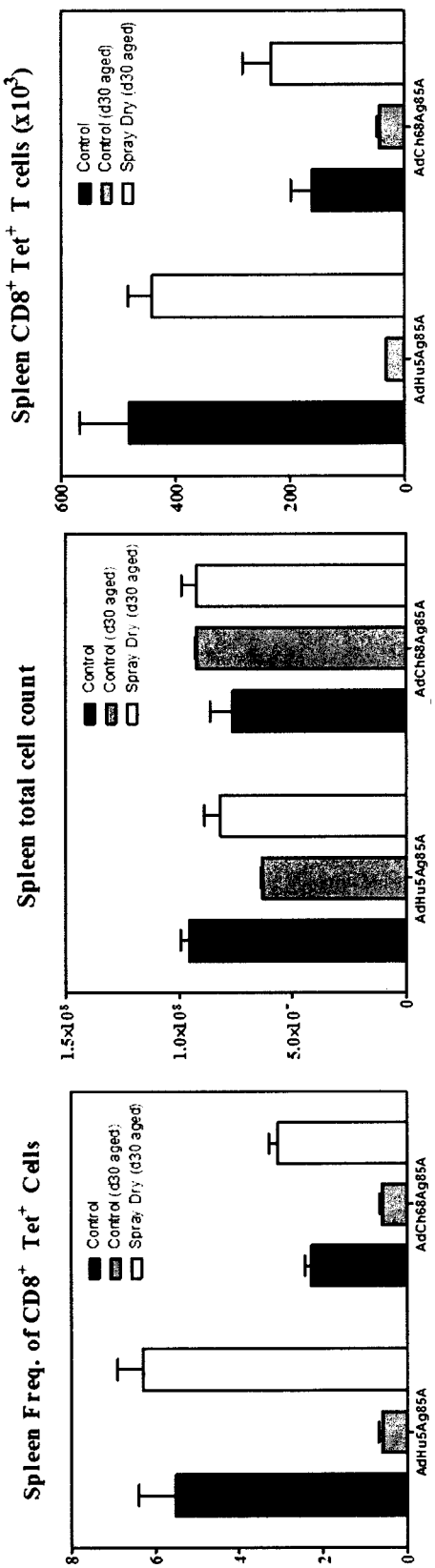
FIG. 14 shows viral infectivity of AdHu5Ag85A and AdCh68Ag85A in the spleen of mice, comparing administration via a PBS solution and a reconstituted exemplary composition of the application 30 days after preparation of the formulations.
Figure 15:
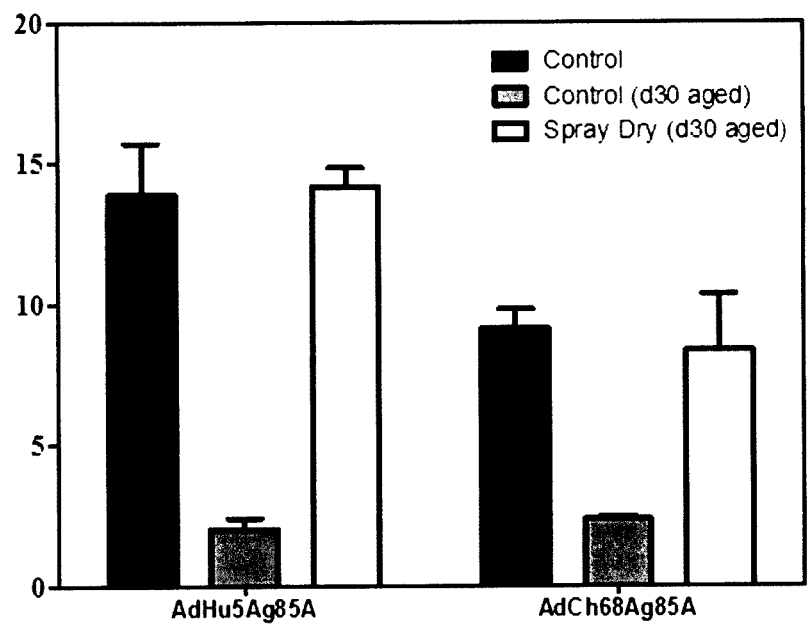
FIG. 15 shows viral infectivity of AdHu5Ag85A and AdCh68Ag85A in the blood of mice, comparing administration via a PBS solution and a reconstituted exemplary composition of the application 30 days after preparation of the formulations.

FIG. 8 shows the loss of AdHu5LacZ infectivity for each spray dried formulation during storage for up to 90 days at 20° C. under moderate moisture conditions (45% RH). By day 90, all formulations were considered to be inactive. This represents a significantly greater viral activity loss at 45% RH compared to <10% RH (noted above) which is attributed to the uptake of water by the spray dried powders within the enclosed storage system. Hygroscopic sugars, and even non-hygroscopic L-leucine particles, will take up detectable quantities of water from the humid air (as demonstrated in FIG. 3). As measured by XRD, the crystallographic profiles for both lactose/trehalose and mannitol/dextran powders showed increasing disorder with water uptake over time. XRD peaks from L-leucine particles exhibited only slight broadening indicating disruption of the initially crystalline spray dried structure. The increase in excipient molecular motion caused by moisture uptake is clearly linked to the destabilization of the adenoviral vector. Matrix destabilization was further emphasized by the decrease in $T_g$ observed for lactose/trehalose and mannitol/dextran samples (Table 5). This significant decrease in $T_g$ indicated a greater molecular mobility within the stored samples. Overall, the increase in moisture resulted in an accelerated rate of viral titre loss. Whereas in drier conditions the rate of titre loss leveled off after approximately ten days (referring to FIG. 7), the same is not observed at 45% RH. This emphasizes the need to store potential AdHu5 vaccines in low humidity environments, however this is more easily maintained than −80° C. temperatures and can be done, for example, using blister packs which are common practice in the pharmaceutical industry.

Overall, the best-performing powder throughout the storage tests, based on retained viral activity, was mannitol/dextran which also encapsulated the adenoviral vector without producing nodules after spray drying (as measured by SEM and XPS). The high $T_g$ for lactose/trehalose particles implied a great thermal stability should have been expected but this was not observed. While not wishing to be limited by theory, this could best be explained through the excipient matrix instability as observed through XRD (FIG. 4*b*). The glass-like state is known to be thermodynamically unfavourable as the polymer glass is being held with a higher volume and entropy than its equilibrium state.[69,70] Physical aging of amorphous and semicrystalline materials can potentially cause a slow relaxation to a more thermodynamically favourable state, even at temperatures below the glass transition.[69] This change occurs more significantly in lactose/trehalose particles than mannitol/dextran particles. These molecular movements result in a greater loss of adenoviral vector function throughout storage. Although similar instability is not observed for L-leucine through XPS, a failure to properly incorporate the AdHu5LacZ vector within the matrix renders it a poor excipient formulation for long term storage.

Viral Infectivity at Elevated Temperatures

Generally, the mannitol/dextran formulation outperformed the other excipients in its ability to retain adenoviral vector activity under mild storage conditions. This formulation was thus subsequently used to test the thermal stability of AdHu5LacZ at more extreme temperatures of 37° C., 45° C. and 55° C. (<10% RH in all cases). As shown in FIG. 9, spray drying adenoviral vector with the mannitol/dextran formulation was found to thermally stabilize the virus significantly more than the liquid control after 72 hours of storage at increased temperatures ($p<0.05$). For the liquid control, there was no measurable AdHu5LacZ activity after 30 minutes at 45° C., or for any harsher storage conditions. In contrast, the mannitol/dextran formulation exhibited good activity after 72 hours at both 37° C. and 45° C. Only at a storage temperature of 55° C. was there a significant loss of viral infectivity after 72 hours for the mannitol/dextran particles due to the increase in energy within the system, which promotes viral protein unfolding.[71,72] This effect is more pronounced in liquid control samples because there is more molecular movement possible. It is presumed from these results that the mannitol/dextran matrix sufficiently restricts the molecular-scale movements of AdHu5LacZ through immobilization within the vitrified particle.

Example 2: In Vivo Testing of Spray Dried Particles

Six- to eight-week-old female BALB/c mice were purchased from Charles River Laboratories (Quebec, Canada) and kept within specific pathogen-free conditions at the McMaster University Central Animal Facility throughout the duration of each experiment. The viral vector was delivered intramuscularly through two separate 50 μL injections in each hind leg for both positive controls and spray dried samples. Positive controls consisted of $1\times10^7$ PFU of AdHu5Ag85A (human) or AdCh68Ag85A (chimpanzee) diluted in 100 μL of PBS. Spray dried samples were 10 mg of mannitol/dextran (67%/33% w/w) powder (viral vector loading of $2\times10^6$ PFU/mg powder) reconstituted in 100 μL of PBS. The viral vectors used through spray drying were equivalent to those in the positive control. Mice were sacrificed fourteen days post-infection and the vaccine efficacy was measured.

FIGS. 10-15 show the results of the in vivo testing of the spray dried mannitol/dextran formulation compared to positive controls. Similar viral infectivity between unprocessed and spray dried viral vaccines was observed in the lung (FIG. 10), spleen (FIG. 11) and blood (FIG. 12) for samples used immediately after preparation (d0). For samples aged 30 days prior to administration, only the spray dried mannitol/dextran formulation retained activity (see FIGS. 13-15).

Example 3: Effect of Weight Ratio of Mannitol and Dextran

Alternate spray dried formulations of AdHu5 entrapped in excipient matrices containing different weight ratios of mannitol and dextran were prepared as described in Example 1. Therefore excipient compositions containing 85% (w/w) mannitol and 40% (w/w) and 60% (w/w) mannitol and 15% (w/w) were prepared and the activity of the adenovirus immediately after preparation was compared with that of the adenovirus formulated in an excipient containing 67% (w/w) mannitol and 33% (w/w).

As can be seen from the results shown in Table 8, the 67%/33% composition was optimal, followed by the 40%/60% composition and the 15%/85%.

TABLE 8

| Sample | Percent Active Viral Vector (%) |
|---|---|
| 85% Mannitol/15% Dextran | 1.66-7.41 |
| 66% Mannitol/33% Dextran | 39.81-63.09 |
| 40% Mannitol/60% Dextran | 22.39-51.29 |

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

REFERENCES (1) Zhu, F.; Hou, L.; Li, J.; Wu, S.; Liu, P.; Zhang, G.; Hu, Y.; Meng, F.; Xu, J.; Tang, R.; Zhang, J. Safety and Immunogenicity of a Novel Recombinant Adenovirus Type-5 Vector-Based Ebola Vaccine in Healthy Adults in China: Preliminary Report of a Randomised, Double-Blind, Placebo-Controlled, Phase 1 Trial. *Lancet* 2015, 6736 (15), 1-8.

(2) Majhen, D.; Calderon, H.; Chandra, N.; Fajardo, C. A.; Rajan, A.; Alemany, R.; Custers, J. Adenovirus-Based Vaccines for Fighting Infectious Diseases and Cancer: Progress in the Field. *Hum. Gene Ther.* 2014, 25 (4), 301-317.

(3) Lasaro, M. O.; Ertl, H. C. J. New Insights on Adenovirus as Vaccine Vectors. *Mol. Ther.* 2009, 17 (8), 1333-1339.

(4) Havenga, M.; Vogels, R.; Zuijdgeest, D.; Radosevic, K.; Mueller, S.; Sieuwerts, M.; Weichold, F.; Damen, I.; Kaspers, J.; Lemckert, a.; van Meerendonk, M.; van der Vlugt, R.; Holterman, L.; Hone, D.; Skeiky, Y.; Mintardjo, R.; Gillissen, G.; Barouch, D.; Sadoff, J.; Goudsmit, J. Novel Replication-Incompetent Adenoviral B-Group Vectors: High Vector Stability and Yield in PER.C6 Cells. *J. Gen. Virol.* 2006, 87 (8), 2135-2143.

(5) Amalfitano, A.; Hauser, M. A.; Hu, H.; Serra, D.; Begy, C. R.; Chamberlain, J. S. Production and Characterization of Improved Adenovirus Vectors with the E1, E2b, and E3 Genes Deleted. *J. Virol.* 1998, 72 (2), 926-933.

(6) Nyberg-Hoffman, C.; Aguilar-Cordova, E. Instability of Adenoviral Vectors during Transport and Its Implication for Clinical Studies. 1999, 955-957.

(7) Rexroad, J.; Martin, T. T.; McNeilly, D.; Godwin, S.; Middaugh, C. R. Thermal Stability of Adenovirus Type 2 as a Function of pH. *J. Pharm. Sci.* 2006, 95 (7), 1469-1479.

(8) Rexroad, J.; Wiethoff, C. M.; Green, A. P.; Kierstead, T. D.; Scott, M. O.; Middaugh, C. R. Structural Stability of Adenovirus Type 5. 2003, 92 (3), 665-678.

(9) Kumru, O. S., Joshi, S. B.; Smith, D. E.; Middaugh, C. R.; Prusik, T.; Volkin, D. B. Vaccine Instability in the Cold Chain: Mechanisms, Analysis and Formulation Strategies. *Biologicals* 2014, 42 (5), 237-259.

(10) World Health Organization. Global Vaccine Action Plan 2011-2020. WHO 2011, pp 1-147.

(11) Crowe, J. H.; Oliver, A. E.; Hoekstra, F. A.; Crowe, L. M. Stabilization of Dry Membranes by Mixtures of Hydroxyethyl Starch and Glucose: The Role of Vitrification. *Cryobiology* 1997, 35 (1), 20-30.

(12) Amorij, J.-P.; Huckriede, A.; Wilschut, J.; Frijlink, H. W.; Hinrichs, W. L. J. Development of Stable Influenza Vaccine Powder Formulations: Challenges and Possibilities. *Pharm. Res.* 2008, 25 (6), 1256-1273.

(13) Alcock, R.; Cottingham, M. G.; Rollier, C. S.; Furze, J.; De Costa, S. D.; Hanlon, M.; Spencer, A. J.; Honeycutt, J. D.; Wyllie, D. H.; Gilbert, S. C.; Bregu, M.; Hill, A. V. S. Long-Term Thermostabilization of Live Poxviral and Adenoviral Vaccine Vectors at Supraphysiological Temperatures in Carbohydrate Glass. *Sci. Transl. Med.* 2010, 2 (19), 19ra12.

(14) Maa, Y. F.; Ameri, M.; Shu, C.; Payne, L. G.; Chen, D. Influenza Vaccine Powder Formulation Development: Spray-Freeze-Drying and Stability Evaluation. *J. Pharm. Sci.* 2004, 93 (7), 1912-1923.

(15) Yu, L. Amorphous Pharmaceutical Solids: Preparation, Characterization and Stabilization. *Adv. Drug Deliv. Rev.* 2001, 48 (1), 27-42.

(16) Ihnat, P. M.; Vellekamp, G.; Obenauer-Kutner, L. J.; Duan, J.; Han, M. a; Witchey-Lakshmanan, L. C.; Grace, M. J. Comparative Thermal Stabilities of Recombinant Adenoviruses and Hexon Protein. *Biochim. Biophys. Acta* 2005, 1726 (2), 138-151.

(17) Hancock, B. C.; Zografi, G. The Use of Solution Theories for Predicting Water Vapor Absorption by Amorphous Pharmaceutical Solids: A Test of the Flory-Huggins and Vrentas Models. *Pharmaceutical Research*. 1993, pp 1262-1267.

(18) Ahlneck, C.; Zografi, G. The Molecular Basis of Moisture Effects on the Physical and Chemical Stability of Drugs in the Solid State. *Int. J. Pharm.* 1990, 62 (2-3), 87-95.

(19) Couchman, P. R. Compositional Variation of Glass Transition Temperatures. 2. Application of the Thermodynamic Theory to Compatible Polymer Blends. *Macromolecules* 1978, 11 (6), 1156-1161.

(20) Penning, J. P.; St. John Manley, R. Miscible Blends of Two Crystalline Polymers. 2. Crystallization Kinetics and Morphology in Blends of Poly(vinylidene Fluoride) and Poly(1,4-Butylene Adipate). *Macromolecules* 1996, 29 (1), 84-90.

(21) Mizuno, A.; Mitsuiki, M.; Motoki, M. Effect of Crystallinity on the Glass Transition Temperature of Starch. *J. Agric. Food Chem.* 1998, 46 (97), 98-103.

(22) Mihranyan, A.; Llagostera, A. P.; Karmhag, R.; Strømme, M.; Ek, R. Moisture Sorption by Cellulose Powders of Varying Crystallinity. *Int. J. Pharm.* 2004, 269 (2), 433-442.

(23) Bronlund, J.; Paterson, T. Moisture Sorption Isotherms for Crystalline, Amorphous and Predominantly Crystalline Lactose Powders. *Int. Dairy J.* 2004, 14 (3), 247-254.

(24) Wong, Y.-L.; Sampson, S.; Germishuizen, W. A.; Goonesekera, S.; Caponetti, G.; Sadoff, J.; Bloom, B. R.; Edwards, D. Drying a Tuberculosis Vaccine without Freezing. *Proc. Natl. Acad. Sci. U.S.A.* 2007, 104 (8), 2591-2595.

(25) Ohtake, S.; Martin, R. a; Yee, L.; Chen, D.; Kristensen, D. D.; Lechuga-Ballesteros, D.; Truong-Le, V. Heat-Stable Measles Vaccine Produced by Spray Drying. *Vaccine* 2010, 28 (5), 1275-1284.

(26) Jin, T. H.; Tsao, E.; Goudsmit, J.; Dheenadhayalan, V.; Sadoff, J. Stabilizing Formulations for Inhalable Powders of an Adenovirus 35-Vectored Tuberculosis (TB) Vaccine (AERAS-402). *Vaccine* 2010, 28 (27), 4369-4375.

(27) Ré, M. I. Microencapsulation By Spray Drying. *Dry. Technol.* 1998, 16 (6), 1195-1236.

(28) Garmise, R. J.; Staats, H. F.; Hickey, A. J. Novel Dry Powder Preparations of Whole Inactivated Influenza Virus for Nasal Vaccination. *AAPS Pharm Sci Tech* 2007, 8 (4), E81.

(29) Saluja, V.; Amorij, J. P.; Kapteyn, J. C.; de Boer, a. H.; Frijlink, H. W.; Hinrichs, W. L. J. A Comparison between Spray Drying and Spray Freeze Drying to Produce an Influenza Subunit Vaccine Powder for Inhalation. *J. Control. Release* 2010, 144 (2), 127-133.

(30) Smaill, F.; Jeyanathan, M.; Smieja, M.; Medina, M. F.; Thanthrige-Don, N.; Zganiacz, A.; Yin, C.; Heriazon, A.; Damjanovic, D.; Puri, L.; Hamid, J.; Xie, F.; Foley, R.; Bramson, J.; Gauldie, J.; Xing, Z. A Human Type 5 Adenovirus-Based Tuberculosis Vaccine Induces Robust T Cell Responses in Humans despite Preexisting Anti-Adenovirus Immunity. *Sci. Transl. Med.* 2013, 5 (205), 205ra134.

(31) Frahm, N.; DeCamp, A. C.; Friedrich, D. P.; Carter, D. K.; Defawe, O. D.; Kublin, J. G.; Casimiro, D. R.; Duerr, A.; Robertson, M. N.; Buchbinder, S. P.; Huang, Y.; Spies, G. a.; De Rosa, S. C.; McElrath, M. J. Human Adenovirus-Specific T Cells Modulate HIV-Specific T Cell Responses to an Ad5-Vectored HIV-1 Vaccine. *J. Clin. Invest.* 2012, 122 (1), 359-367.

(32) Appaiahgari, M. B.; Vrati, S. Adenoviruses as Gene/vaccine Delivery Vectors: Promises and Pitfalls. *Expert Opin. Biol. Ther.* 2014, 2598 (October), 1-15.

(33) Richardson, J. S.; Abou, M. C.; Tran, K. N.; Kumar, A.; Sahai, B. M.; Kobinger, G. P. Impact of Systemic or Mucosal Immunity to Adenovirus on Ad-Based Ebola Virus Vaccine Efficacy in Guinea Pigs. *J. Infect. Dis.* 2011, 204 Suppl (Suppl 3), S1032-S1042.

(34) Xing, Z.; Ohkawara, Y.; Jordana, M.; Graham, F. L.; Gauldie, J. Transfer of Granulocyte-Macrophage Colony-Stimulating Factor Gene to Rat Lung Induces Eosinophilia, Monocytosis, and Fibrotic Reactions. *J. Clin. Invest.* 1996, 97 (4), 1102-1110.

(35) Abràmoff, M. D.; Magalhães, P. J.; Ram, S. J. Image Processing with image *J. Biophotonics Int.* 2004, 11 (7), 36-41.

(36) Williams, K. R.; Gupta, K.; Wasilik, M. Etch Rates for Micromachining Processing—Part II. *J. Microelectromechanical Syst.* 2003, 12 (6), 761-778.

(37) Mazzobre, M. F.; Soto, G.; Aguilera, J. M.; Buera, M. P. Crystallization Kinetics of Lactose in Sytems Co-Lyofilized with Trehalose. Analysis by Differential Scanning calorimetry. *Food Res. Int.* 2001, 34 (10), 903-911.

(38) Reed, L.; Muench, H. A Simple Method of Estimating Fifty percent Endpoints. *Am. J. Epidemiol.* 1938, 27 (3), 493-497.

(39) Gliński, J.; Chavepeyer, G.; Platten, J. K. Surface Properties of Aqueous Solutions of L-Leucine. *Biophys. Chem.* 2000, 84 (2), 99-103.

(40) Vehring, R. Pharmaceutical Particle Engineering via Spray Drying. *Pharm. Res.* 2008, 25 (5), 999-1022.

(41) Elversson, J.; Millqvist-Fureby, A. Particle Size and Density in Spray Drying-Effects of Carbohydrate Properties. *J. Pharm. Sci.* 2005, 94 (9), 2049-2060.

(42) Newman, A. W.; Reutzel-Edens, S. M.; Zografi, G. Characterization of the "Hygroscopic" Properties of Active Pharmaceutical Ingredients. *Journal of Pharmaceutical Sciences.* 2008, pp 1047-1059.

(43) Hancock, B. C.; Zografi, G. The Relationship Between the Glass Transition Temperature and the Water Content of Amorphous Pharmaceutical Solids. *Pharm. Res.* 1994, 11 (4), 471-477.

(44) Raula, J.; Thielmann, F.; Kansikas, J.; Hietala, S.; Annala, M.; Seppälä, J.; Lände, A.; Kauppinen, E. I. Investigations on the Humidity-Induced Transformations of Salbutamol Sulphate Particles Coated with L-Leucine. *Pharm. Res.* 2008, 25 (10), 2250-2261.

(45) Raula, J.; Kurkela, J. a.; Brown, D. P.; Kauppinen, E. I. Study of the Dispersion Behaviour of L-Leucine Containing Microparticles Synthesized with an Aerosol Flow Reactor Method. *Powder Technol.* 2007, 177 (3), 125-132.

(46) Naini, V.; Byron, P. R.; Phillips, E. M. Physicochemical Stability of Crystalline Sugars and Their Spray-Dried Forms: Dependence upon Relative Humidity and Suitability for Use in Powder Inhalers. *Drug Dev. Ind. Pharm.* 1998, 24 (10), 895-909.

(47) Lehto, V.-P., Tenho, M.; Vähä-Heikkilä, K.; Harjunen, P.; Päällysaho, M.; Välisaari, J.; Niemelä, P.; Järvinen, K. The Comparison of Seven Different Methods to Quantify the Amorphous Content of Spray Dried Lactose. *Powder Technol.* 2006, 167 (2), 85-93.

(48) Banno, N.; Nakanishi, T.; Matsunaga, M.; Asahi, T.; Osaka, T. Enantioselective Crystal Growth of Leucine on a Self-Assembled Monolayer with Covalently Attached Leucine Molecules. 2004, 428-429.

(49) Sundaramurthi, P.; Suryanarayanan, R. Trehalose Crystallization During Freeze-Drying: Implications On Lyoprotection. *J. Phys. Chem. Lett.* 2010, 1 (2), 510-514.

(50) Lerk, C. F. Consoloidation and Compaction of Lactose. *Drug Dev. Ind. Pharm.* 1993, 19 (17), 2359-2398.

(51) Miao, S.; Roos, Y. Crystallization Kinetics and X-ray Diffraction of Crystals Formed in Amorphous Lactose, Trehalose, and Lactose/Trehalose Mixtures. *J. Food Sci.* 2005, 70 (5), 350-358.

(52) Ding, S.-P., Fan, J.; Green, J. L.; Lu, Q.; Sanchez, E.; Angell, C. a. Vitrification of Trehalose by Water Loss from Its Crystalline Dihydrate. *J. Therm. Anal.* 1996, 47 (5), 1391-1405.

(53) Willart, J. F.; De Gusseme, a.; Hemon, S.; Descamps, M.; Leveiller, F.; Rameau, a. Vitrification and Polymorphism of Trehalose Induced by Dehydration of Trehalose Dihydrate. *J. Phys. Chem. B* 2002, 106 (13), 3365-3370.

(54) Saleki-Gerhardt, A.; Stowell, J. G.; Byrn, S. R.; Zografi, G. Hydration and Dehydration of Crystalline and Amorphous Forms of Raffinose. *J. Pharm. Sci.* 1995, 84 (3), 318-323.

(55) Vehring, R.; Foss, W. R.; Lechuga-Ballesteros, D. Particle Formation in Spray Drying. *J. Aerosol Sci.* 2007, 38 (7), 728-746.

(56) Rani, M.; Govindarajan, R.; Surana, R.; Suryanarayanan, R. Structure in Dehydrated Trehalose Dihydrate—Evaluation of the Concept of Partial Crystallinity. *Pharm. Res.* 2006, 23 (10), 2356-2367.

(57) Taylor, N. W.; Zobel, H. F.; Hellman, N. N.; Senti, F. R. Effect of Structure and Crystallinity on Water Sorption of Dextran. *J. Phys. Chem* 1959, 63 (4), 599-603.

(58) Hulse, W. L.; Forbes, R. T.; Bonner, M. C.; Getrost, M. The Characterization and Comparison of Spray-Dried Mannitol Samples. *Drug Dev. Ind. Pharm.* 2009, 35 (6), 712-718.

(59) Kim, A. I.; Akers, M. J.; Nail, S. L. The Physical State of Mannitol after Freeze-Drying: Effects of Mannitol Concentration, Freezing Rate, and a Noncrystallizing Cosolute. *J. Pharm. Sci.* 1998, 87 (8), 931-935.

(60) Martins, T. S.; Matos, J. R.; Vicentini, G.; Isolani, P. C. Synthesis, Characterization, Spectroscopy and Thermal Analysis of Rare Earth Picrate Complexes with L-Leucine. *J. Therm. Anal. Calorim.* 2006, 86 (2), 351-357.
(61) Listiohadi, Y.; Hourigan, J. A.; Sleigh, R. W.; Steele, R. J. Thermal Analysis of Amorphous Lactose and α-Lactose Monohydrate. *Dairy Sci. Technol.* 2009, 89 (1), 43-67.
(62) Kennedy, M. A.; Parks, R. J. Adenovirus Virion Stability and the Viral Genome: Size Matters. *Mol. Ther.* 2009, 17 (10), 1664-1666.
(63) Jackson, K. A. Crystal Growth Kinetics. *Mater. Sci. Eng.* 1984, 65 (1), 7-13.
(64) Green, M.; Pina, M. Biochemical Studies on Adenovirus Multiplication. IV. Isolation, Purification, and Chemical Analysis of Adenovirus. *Virology* 1963, 20, 199-207.
(65) Pina, M.; Green, M. Biochemical Studies on Adenovirus Multiplication, IX. Chemical and Base Composition Analysis of 28 Human Adenoviruses. *Proc. Natl. Acad. Sci. U.S.A.* 1965, 54 (2), 547-551.
(66) Mazzobre, M. F.; del Pilar Buera, M.; Chirife, J. Protective Role of Trehalose on Thermal Stability of Lactase in Relation to Its Glass and Crystal Forming Properties and Effect of Delaying Crystallization. *LWT—Food Sci. Technol.* 1997, 30 (3), 324-329.
(67) Crowe, L. M.; Reid, D. S.; Crowe, J. H. Is Trehalose Special for Preserving Dry Biomaterials? *Biophys. J.* 1996, 71 (4), 2087-2093.
(68) Uedaira, H.; Uedaira, H. Sugar-Water Interaction from Diffusion Measurements. *J. Solution Chem.* 1985, 14 (1), 27-34.
(69) Struik, L. C. E. Physical Aging in Plastics and Other Glassy Materials. *Polym. Eng. Sci.* 1977, 17 (3), 165-173.
(70) Farhoodi, M.; Mousavi, S. M.; Oromiehie, A.; Mansour, H. A Study on Physical Aging of Semicrystalline Terephthalate below the Glass Transition Point Polyethylene. *J. Appl. Res. Technol.* 2012, 10 (October), 698-702.
(71) Pace, C. N.; Vanderburg, K. E. Determining Globular Protein Stability: Guanidine Hydrochloride Denaturation of Myoglobin. *Biochemistry* 1979, 18 (2), 288-292.
(72) Pace, C. N.; Hermans, J. The Stability of Globular Proteins. *Crit. Rev. Biochem. Mol. Biol.* 1975, 3 (1), 1-43.

The invention claimed is:

1. An adenovirus composition comprising adenovirus particles and an excipient, wherein the excipient comprises a mixture of dextran and mannitol in amounts effective to maintain at least 40% of the adenovirus activity after spray drying,
wherein the excipient comprises about 60 wt % to about 75 wt % of the mannitol and/or the excipient comprises about 25 wt % to about 40 wt % dextran.

2. The adenovirus composition of claim 1, wherein the adenovirus is a recombinant DNA adenovirus.

3. The adenovirus composition of claim 1, wherein the excipient comprises a mixture of dextran and mannitol in amounts effective to maintain at least 50% of the adenovirus activity after spray drying.

4. The adenovirus composition of claim 1, wherein the excipient comprises a mixture of dextran and mannitol in amounts effective to maintain at least 40% of the adenovirus activity after spray drying and storage at 20° C., less than 10% relative humidity (RH) and for at least 90 days.

5. The adenovirus composition of claim 1, further comprising a pharmaceutically acceptable carrier.

6. The adenovirus composition of claim 1, which has been spray dried.

7. The adenovirus composition of claim 1, wherein the change in adenovirus infectivity following spray drying and storage at 20° C., <10% RH and for 90 days is less than 1.0 log unit.

8. A method for preparing the adenovirus composition of claim 1 comprising:
a) combining the adenovirus with an aqueous solution comprising an excipient, wherein the excipient comprises a mixture of dextran and mannitol in amounts effective to maintain at least 40% of the adenovirus activity after spray drying to provide a mixture; and
b) spray drying the mixture to provide the adenovirus composition.

9. The method of claim 8, wherein the aqueous solution comprising the excipient is prepared by dissolving the dextran and mannitol in an aqueous solution at a concentration in the range of about 0.1 mg excipient per mL of water to about 10 mg excipient per mL of water.

10. The method of claim 8, wherein the aqueous solution comprising the excipient has a pH of about 6 to about 7.

11. The method of claim 8, wherein the excipient comprises a mixture of dextran and mannitol in amounts effective to maintain at least 30% of the adenovirus activity after spray drying and storage at 20° C., less than 10% RH and for at least 90 days.

12. The method of claim 8, wherein the excipient comprises about 60 wt % to about 75 wt % of the mannitol.

13. The method of claim 8, wherein the excipient comprises about 25 wt % to about 40 wt % dextran.

14. The method of claim 8, wherein the change in adenovirus infectivity following spray drying and storage at 20° C., <10% RH and for 90 days is less than 1.0 log unit.

15. The method of claim 8, further comprising the step of processing the stabilized adenovirus composition into a formulation suitable for administration as a liquid injection, or processing the stabilized adenovirus composition into a formulation suitable for administration via ingestion, inhalation or via pulmonary delivery.

16. A stabilized spray dried adenovirus composition prepared using the method of claim 8.

17. A method for delivering or transferring one or more nucleic acid sequences to target cells comprising administering an effective amount of an adenovirus composition of claim 1 to the cells.

18. A method for treating a subject with a vaccine comprising administering an effective amount of an adenovirus composition of claim 1 to a subject in need thereof.

19. A method for gene therapy comprising administering an effective amount of an adenovirus composition of claim 1 to a subject in need thereof.

* * * * *